US010449096B2

(12) United States Patent
Hayashi et al.

(10) Patent No.: US 10,449,096 B2
(45) **Date of Patent: *Oct. 22, 2019**

(54) ABSORBENT ARTICLE MANUFACTURING APPARATUS AND METHOD FOR MODIFYING MANUFACTURING APPARATUS

(71) Applicant: UNICHARM Corporation, Ehime (JP)

(72) Inventors: Tomoki Hayashi, Kagawa (JP); Hidetaka Oyama, Kagawa (JP); Jun Okuda, Kagawa (JP); Satoshi Mitsuno, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 564 days.

This patent is subject to a terminal disclaimer.

(21) Appl. No.: 15/029,626

(22) PCT Filed: Sep. 22, 2014

(86) PCT No.: PCT/JP2014/075115
§ 371 (c)(1),
(2) Date: Apr. 14, 2016

(87) PCT Pub. No.: WO2015/056535
PCT Pub. Date: Apr. 23, 2015

(65) Prior Publication Data

US 2016/0228301 A1 Aug. 11, 2016

(30) Foreign Application Priority Data

Oct. 18, 2013 (JP) ................................ 2013-217215

(51) Int. Cl.
*A61F 13/15* (2006.01)
*A01K 1/015* (2006.01)
(Continued)

(52) U.S. Cl.
CPC ...... *A61F 13/15731* (2013.01); *A01K 1/0157* (2013.01); *A61F 13/15699* (2013.01);
(Continued)

(58) Field of Classification Search
CPC ......... A61F 13/15731; A61F 13/15699; A01K 1/0107; A01K 1/0157; D06C 7/00;
(Continued)

(56) References Cited

U.S. PATENT DOCUMENTS 2,772,486 A * 12/1956 Johanson .................. D21F 5/00 34/223
3,228,114 A * 1/1966 Smith, Jr. ............... F26B 3/283 34/561

(Continued)

FOREIGN PATENT DOCUMENTS

CN 1394561 A 2/2003
CN 1407305 A 4/2003

(Continued)

OTHER PUBLICATIONS

Office Action in EP Application No. 14854715.1, dated Jun. 28, 2017.

(Continued)

*Primary Examiner* — Stephen F. Gerrity
*Assistant Examiner* — Joshua G Kotis
(74) *Attorney, Agent, or Firm* — Hauptman Ham, LLP

(57) ABSTRACT

An absorbent article manufacturing apparatus includes: a first conveying route that is arranged in a straight line along a first direction in plan view; a plurality of processing devices that process an intermediate product of an absorbent article that is conveyed along the first conveying route; and a heating unit that restores bulk of a non-woven fabric through heating the non-woven fabric by blowing hot air onto the non-woven fabric while conveying the non-woven (Continued)

fabric along a direction in which the non-woven fabric is continuous, the non-woven fabric being a strip shape and serving as a part of the absorbent article. In a case where a direction that intersects the first direction in plan view is set as a second direction, the heating unit is arranged in one of a position that is directly above the first conveying route and a position that is displaced from the first conveying route to the second direction.

8 Claims, 11 Drawing Sheets

(51) Int. Cl.
*D06C 7/00* (2006.01)
*A01K 1/01* (2006.01)

(52) U.S. Cl.
CPC .............. *D06C 7/00* (2013.01); *A01K 1/0107* (2013.01); *A61F 13/15203* (2013.01); *A61F 2013/15821* (2013.01)

(58) Field of Classification Search
CPC ... D06C 7/02; D06C 7/04; D06B 3/12; D06B 5/08; F27B 9/28; F27B 9/36; F26B 13/06; F26B 13/08
USPC .......... 119/169, 171, 172; 19/66 R; 493/467; 156/282, 322, 276; 442/393; 432/8, 59
See application file for complete search history.

(56) References Cited

U.S. PATENT DOCUMENTS 3,281,205 A * 10/1966 Runton .................. D03D 15/08 139/421
3,458,905 A * 8/1969 Dodson, Jr. .......... B65H 69/066 28/104
3,477,138 A * 11/1969 Snow ...................... F26B 13/08 34/464
3,906,755 A * 9/1975 Sando .................... D06B 21/00 28/155
4,052,796 A 10/1977 Arendt
4,124,941 A * 11/1978 Birke ...................... F26B 13/08 34/421
4,342,718 A 8/1982 Caratsch
4,800,656 A * 1/1989 Brosch .................... F26B 13/08 34/242
4,952,145 A * 8/1990 Kwiatkowski .......... B29C 35/06 126/92 AC
5,471,766 A * 12/1995 Heikkila ............... F26B 13/104 34/461
5,791,030 A * 8/1998 Aihara .................... B29C 55/08 26/100
5,908,290 A * 6/1999 Kawamura ............... D01F 9/32 34/636
6,397,444 B1 * 6/2002 Foster ...................... D02G 1/02 28/220
7,268,323 B2 * 9/2007 Tomobe .................. B29C 71/02 219/388
9,903,058 B2 * 2/2018 Okuda .............. A61F 13/15764
2002/0193765 A1 12/2002 Kudo et al.
2004/0010895 A1 1/2004 Vonfeldt et al.
2004/0111848 A1 6/2004 Miyamoto et al.
2004/0214124 A1 * 10/2004 Stockhausen ............. D01F 9/32 432/59
2011/0191994 A1 * 8/2011 Takahashi ............. D04H 1/498 28/167
2013/0171578 A1 * 7/2013 Berner ...................... D01F 9/32 432/199
2013/0174379 A1 * 7/2013 Ishino ............... A61F 13/15707 19/98
2015/0067996 A1 * 3/2015 Okuda ..................... D04H 1/50 26/106
2015/0211157 A1 7/2015 Okuda et al.

FOREIGN PATENT DOCUMENTS

CN 1497086 A 5/2004
CN 102373595 A 3/2012
JP 5-35856 U 5/1993
JP H6-158499 A 6/1994
JP 11-504228 A 4/1999
JP 2003-291234 A 10/2003
JP 2003-339761 A 12/2003
JP 2004-137655 A 5/2004
JP 2008-100110 A 5/2008
JP 2010-156075 A 7/2010
JP 2010-156076 A 7/2010
JP 2011-212211 A 10/2011

OTHER PUBLICATIONS

Office Action in EP Application No. 14854715.1, dated Feb. 5, 2018, 3pp.
Written Opinion in International Patent Application No. PCT/JP2014/075115 dated Nov. 25, 2014.
International Search Report in PCT/JP2014/075115, dated Nov. 25, 2014.
Extended European Search Report in EP Application No. 14854715.1 dated Aug. 16, 2016.
Office Action in JP Application No. 2015-094040, dated Oct. 10, 2017, 3pp.
Office Action in EP Application No. 14854316.8, dated Jun. 22, 2017, 3pp.
Office Action in JP Application No. 2015-094040, dated Apr. 25, 2017, 3pp.
Extended European Search Report in EP Application No. 14854316.8, dated Aug. 3, 2016, 6pp.
Written Opinion of the ISA in PCT/JP2014/075103, dated Nov. 25, 2014, 9pp.
International Search Report in PCT/JP2014/075103, dated Nov. 25, 2014, 4pp.

* cited by examiner

ABSORBENT ARTICLE MANUFACTURING APPARATUS AND METHOD FOR MODIFYING MANUFACTURING APPARATUS

RELATED APPLICATIONS

The present application is a National Phase entry of International Application No. PCT/JP2014/075115, filed Sep. 22, 2014, which claims priority of Japanese Application No. 2013-217215, filed Oct. 18, 2013.

TECHNICAL FIELD

The present invention relates to an absorbent article manufacturing apparatus of an absorbent article such as a pet sheet, and a method for modifying a manufacturing apparatus.

BACKGROUND ART

Conventionally, sanitary napkins and disposable diapers have been used as absorbent articles. Pet sheets, which are included in the same category, are also widely used as a toilet for pets.

A liquid-permeable top sheet is provided in the portions of such absorbent articles that come into contact with the user's skin or the like. Furthermore, recently, high liquid draining performance has been demanded for top sheets from the viewpoint of reducing the sense of stickiness to skin for example, and bulky non-woven fabric is considered to be favorable as such a material.

Such non-woven fabric is manufactured in a strip-shape using an appropriate method such as carding, and then wound into a roll and stored in the form of a non-woven fabric whole cloth. When the time to be used arrives, the non-woven fabric whole cloth is carried to the absorbent article manufacturing line, and the non-woven fabric is fed from the whole cloth in the line and used as the top sheet material.

When non-woven fabric is wound into a non-woven fabric whole cloth, tension is applied in the winding direction during winding to prevent the non-woven fabric from zigzagging or the like. For this reason, non-woven fabric is normally wound tightly due to this tension. Specifically, the non-woven fabric is compressed in the thickness direction and has reduced bulk. Accordingly, when the non-woven fabric is fed from the non-woven fabric whole cloth in the absorbent article manufacturing line, only the non-woven fabric having reduced bulk is fed and supplied, and thus it is not possible to meet the aforementioned demand for bulky non-woven fabric.

To address this problem, Patent Document 1 discloses a technique in which a bulk restoring device is installed upstream in the absorbent article manufacturing line. Specifically, it is disclosed that non-woven fabric fed from a non-woven fabric whole cloth is heated by hot air being blown thereon with a bulk restoring device when the non-woven fabric passes through a predetermined conveying route, and thus the bulk of the non-woven fabric is restored. It is also disclosed that the non-woven fabric after the aforementioned heating is sent as-is to the next processing device in the manufacturing line, without being wound again.

CITATION LIST

Patent Document

[Patent Document 1] JP 2004-137655A

SUMMARY OF INVENTION

Technical Problem

The manufacturing line has a plurality of processing devices for manufacturing absorbent articles, in addition to a bulk restoring device. These processing devices are arranged along a first conveying route along which intermediate products such as absorbent bodies related to absorbent articles are conveyed. Typically, the first conveying route is arranged in a straight line along a predetermined first direction in plan view.

Here, since a heating unit of the bulk restoring device heats the non-woven fabric to restore the bulk, the heating unit itself is at a high temperature and might radiate heat to the environment. Consequently, depending on the position of the heating unit in plan view, the heating unit might have a thermal influence on the intermediate products and the processing devices in the first conveying route, which can be a cause of problems. Specifically, the environmental air heated by the heat radiated with the heating unit travels upward due to the reduced specific gravity thereof. For this reason, supposing that the heating unit is arranged directly below the first conveying route, the heated air travels upward to the intermediate products and the processing devices in the first conveying route directly above the heating unit, and heats the intermediate products and the processing devices, which might cause problems.

The present invention was achieved in light of conventional problems such as those described above, and an object thereof is to effectively prevent a heating unit for restoring the bulk of a non-woven fabric from having a thermal influence on intermediate products and processing devices of absorbent articles.

Solution to Problem

A main aspect of the invention for achieving the aforementioned object is an absorbent article manufacturing apparatus including:

a first conveying route that is arranged in a straight line along a first direction in plan view;

a plurality of processing devices that process an intermediate product of an absorbent article that is conveyed along the first conveying route; and a heating unit that restores bulk of a non-woven fabric through heating the non-woven fabric by blowing hot air onto the non-woven fabric while conveying the non-woven fabric along a direction in which the non-woven fabric is continuous, the non-woven fabric being a strip shape and serving as a part of the absorbent article, in a case where a direction that intersects the first direction in plan view is set as a second direction, the heating unit being arranged in one of a position that is directly above the first conveying route and a position that is displaced from the first conveying route to the second direction.

Another aspect of the invention is a method for modifying a manufacturing apparatus that manufactures an absorbent article by processing an intermediate product of the absorbent article using a plurality of processing devices, the intermediate product being conveyed along a first conveying route that is arranged in a straight line along a first direction in plan view, the method including:

setting a direction that intersects the first direction in plan view as a second direction; and arranging a heating unit in one of a position that is directly above the first conveying route and a position that is displaced from the first conveying route to the second direction, the heating unit restoring bulk of a non-woven fabric through heating the non-woven fabric by blowing hot air onto the non-woven fabric while conveying the non-woven fabric along a direction in which the non-woven fabric is continuous, the non-woven fabric being a strip shape and serving as a part of the absorbent article.

Other features of the present invention will become evident from the description of this specification and the accompanying drawings.

Advantageous Effects of Invention

According to the present invention, it is possible to effectively prevent a heating unit for restoring the bulk of non-woven fabric from having a thermal influence on intermediate products and processing devices related to absorbent articles.

DESCRIPTION OF EMBODIMENTS

Figure 1A:
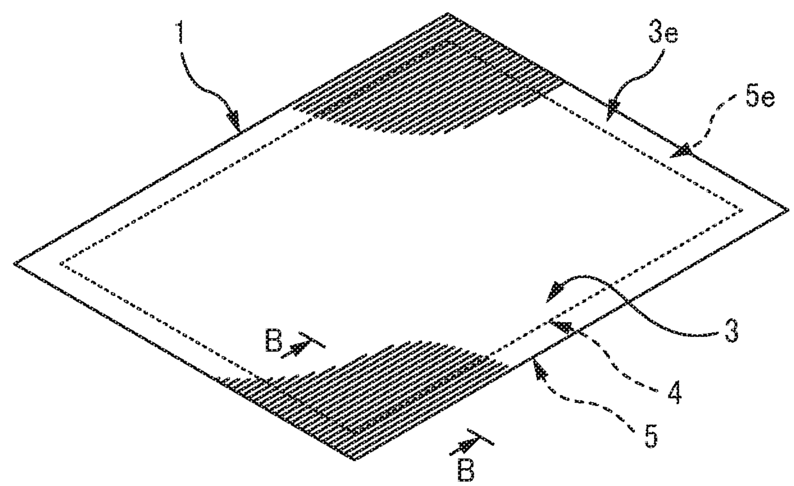
FIG. 1A is an exterior perspective view of a pet sheet 1.

At least the following will become evident from the description of this specification and the accompanying drawings.

An absorbent article manufacturing apparatus including:

a first conveying route that is arranged in a straight line along a first direction in plan view;

a plurality of processing devices that process an intermediate product of an absorbent article that is conveyed along the first conveying route; and a heating unit that restores bulk of a non-woven fabric through heating the non-woven fabric by blowing hot air onto the non-woven fabric while conveying the non-woven fabric along a direction in which the non-woven fabric is continuous, the non-woven fabric being a strip shape and serving as a part of the absorbent article, in a case where a direction that intersects the first direction in plan view is set as a second direction, the heating unit being arranged in one of a position that is directly above the first conveying route and a position that is displaced from the first conveying route to the second direction.

According to this absorbent article manufacturing apparatus, the heating unit is arranged in a position directly above the first conveying route or a position that is displaced from the first conveying route to the second direction. Thus, the heating unit is effectively prevented from having a thermal influence on the intermediate product and the processing devices. Specifically, although the air heated by the heat radiated with the heating unit travels upward due to the reduced specific gravity thereof, the first conveying route does not exist directly above the heating unit. Thus, it is possible to suppress the thermal influence on the intermediate product and the processing devices in the first conveying route, which the heated air might have.

In the above absorbent article manufacturing apparatus, it is preferable that the heating unit is arranged in a position that is displaced from the first conveying route to the second direction, and the non-woven fabric that has been heated with the heating unit and whose bulk has been thus restored is conveyed in the second direction along a second conveying route and is input to the first conveying route.

According to this absorbent article manufacturing apparatus, the non-woven fabric that has been heated with the heating unit and whose bulk has been thus restored is cooled while being conveyed in the second direction along the second conveying route. Thus, the non-woven fabric that has been heated is effectively prevented from having a thermal influence on the intermediate product and the processing devices in the first conveying route.

Also, it is likely that empty space remains in a position that is displaced from the first conveying route to the second direction in plan view. Thus, for example, in the case of adding a heating unit to an existing absorbent article manufacturing apparatus by performing modification work, it is easy to secure a space for installing the heating unit.

In the above absorbent article manufacturing apparatus, it is preferable that the heating unit is arranged directly above the first conveying route, and a conveying route of the non-woven fabric in the heating unit is oriented along a horizontal direction.

According to this absorbent article manufacturing apparatus, the conveying route for the non-woven fabric in the heating unit is oriented along the horizontal direction, and it is thus possible to reduce the vertical dimension of the heating unit. Accordingly, it is possible to prevent problems that can occur due to the heating unit being arranged directly above the first conveying route. For example, if the vertical dimension of the heating unit is large, it tends to interfere with an existing installed objects such as an appropriate duct located above the first conveying route, and according to the above configuration, it is possible to reduce the vertical dimension of the heating unit, thus making it possible to prevent interference with existing installed objects thereabove.

In the above absorbent article manufacturing apparatus, it is preferable that the heating unit has a case member equipped with an entrance for the non-woven fabric and an exit for the non-woven fabric, one of an entrance-side portion and an exit-side portion of the case member has a blast opening that blasts the hot air into a space inside the case member toward another one of the entrance-side portion and the exit-side portion, and the other one of the entrance-side portion and the exit-side portion has a discharge port that discharges, from the case member, the hot air that has flowed while being in contact with one surface of both surfaces of the non-woven fabric.

According to this absorbent article manufacturing apparatus, hot air is blasted from the blast opening so as to flow from one side to the other side in the conveying direction, and the hot air heats the non-woven fabric while being in contact with one of both surfaces of the non-woven fabric as it flows from the one side to the other side. Accordingly, the bulk of the non-woven fabric can be reliably restored.

Also, because the hot air flows over the surface of the non-woven fabric, compression of the non-woven fabric in the thickness direction is effectively prevented. It is thus possible to smoothly perform bulk restoration.

In the above absorbent article manufacturing apparatus, it is preferable that absorbent article manufacturing apparatus further includes a cooling unit that cools the non-woven fabric that has been heated with the hot air, before the non-woven fabric is input to the first conveying route, wherein the cooling unit has a case member equipped with an entrance for the non-woven fabric and an exit for the non-woven fabric, one of an entrance-side portion and an exit-side portion of the case member has a blast opening that blasts cooling wind into a space inside the case member toward another one of the entrance-side portion and the exit-side portion, and the other one of the entrance-side portion and the exit-side portion has a discharge port that discharges, from the case member, the wind that has flowed while being in contact with one surface of both surfaces of the non-woven fabric.

According to this absorbent article manufacturing apparatus, the cooling unit cools the non-woven fabric that was heated by the hot air. Thus, it is possible to more reliably prevent the heated non-woven fabric from having a thermal influence on the intermediate product and the processing devices in the first conveying route.

Also, cooling wind is blasted from the blast opening so as to flow from one side to the other side in the conveying direction, and the cooling wind cools the non-woven fabric while being in contact with one of both surfaces of the non-woven fabric as it flows from the one side to the other side. Accordingly, the non-woven fabric can be reliably cooled.

Furthermore, because the cooling wind flows over the surface of the non-woven fabric, compression of the non-woven fabric in the thickness direction is effectively prevented. Accordingly, the loss of the restored bulk by the cooling wind can be reliably avoided.

A method for modifying a manufacturing apparatus that manufactures an absorbent article by processing an intermediate product of the absorbent article using a plurality of processing devices, the intermediate product being conveyed along a first conveying route that is arranged in a straight line along a first direction in plan view, the method including:

setting a direction that intersects the first direction in plan view as a second direction; and arranging a heating unit in one of a position that is directly above the first conveying route and a position that is displaced from the first conveying route to the second direction, the heating unit restoring bulk of a non-woven fabric through heating the non-woven fabric by blowing hot air onto the non-woven fabric while conveying the non-woven fabric along a direction in which the non-woven fabric is continuous, the non-woven fabric being a strip shape and serving as a part of the absorbent article.

According to this method for modifying an absorbent article manufacturing apparatus, the heating unit is arranged in a position directly above the first conveying route or a position that is displaced from the first conveying route to the second direction. Thus, it is possible to modify the manufacturing apparatus such that the heating unit is unlikely to have a thermal influence on the intermediate product and the processing devices in the first conveying route. Specifically, although the air heated by the heat radiated with the heating unit travels upward due to the reduced specific gravity thereof, the manufacturing apparatus is modified such that the first conveying route does not exist above the heating unit. Thus, with the modified manufacturing device as well, the intermediate product and the processing devices in the first conveying route are prevented from being subjected to a thermal influence.

First Embodiment

An absorbent article manufacturing apparatus 10 according to a first embodiment manufactures a pet sheet 1 as an example of an absorbent article.

Figure 1B:
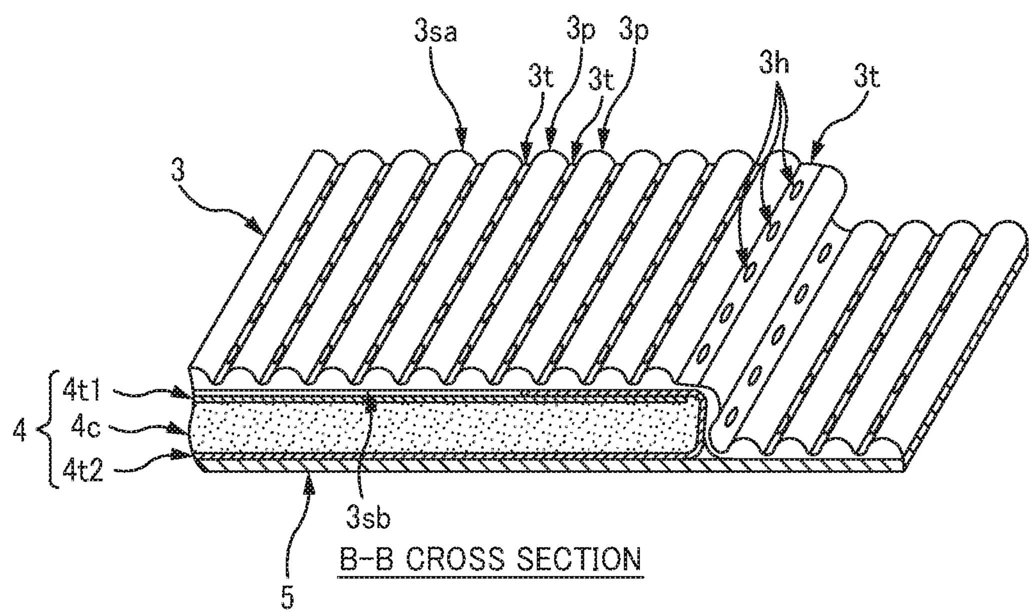
FIG. 1B is an enlarged perspective view of the pet sheet 1 cut along a line B-B in FIG. 1A.

FIG. 1A is an exterior perspective view of the pet sheet 1, and FIG. 1B is an enlarged perspective view of the pet sheet 1 cut along a line B-B in FIG. 1A.

The pet sheet 1 is used in the treatment of excretion from animals such as dogs or cats, and is used in the state of being placed on the floor or the like as shown in FIG. 1A. The pet sheet 1 has a liquid-permeable top sheet 3 that is rectangular in a plan view, a liquid-impermeable back sheet 5 that has roughly the same shape, and a liquid-absorbent absorbent body 4 interposed between the sheets 3 and 5, for example. The absorbent body 4 is joined to both the top sheet 3 and the back sheet 5 using a hot-melt adhesive, and the portions of the top sheet 3 and the back sheet 5 that protrude laterally beyond the absorbent body 4, that is to say peripheral edge portions 3*e* and 5*e* of the sheets 3 and 5, are joined together using the hot-melt adhesive.

It should be noted that the hot-melt adhesive referred to here is a thermoplastic adhesive that can be melted by heat and applied in a fluidized state.

As shown in FIG. 1B, the absorbent body 4 has an absorbent core 4*c*, which is formed by laminating liquid-absorbent fibers such as pulp fibers and superabsorbent polymers (so-called SAP) in an approximately rectangular shape in a plan view, as well as a covering sheet that covers the core 4*c*, for example. The covering sheet is, for example, a liquid-permeable sheet made of tissue paper or the like, and in this example, two covering sheets 4*t*1 and 4*t*2 are provided. Specifically, the core is covered with the one covering sheet 4*t*1 on the skin-side surface, and covered with the other covering sheet 4*t*2 on the non-skin-side surface. In the following description, the former covering sheet on the skin-side surface, that is to say the covering sheet 4*t*1, is referred to as "the skin-side covering sheet 4*t*1", and the latter covering sheet on the non-skin-side surface, that is to say the covering sheet 4_t_2, is referred to as "the non-skin-side covering sheet 4_t_2". It should be noted that both the skin-side surface and the non-skin-side surface may be covered with one covering sheet, and in some cases these covering sheets 4_t_1 and 4_t_2 need not be provided.

The back sheet 5 is a film material made of polyethylene (hereinafter, PE), polypropylene (hereinafter, PP), polyethylene terephthalate (hereinafter, PET), or the like. There is no limitation whatsoever to the above examples, and any liquid-impermeable sheet can be used.

The top sheet 3 is made up of the non-woven fabric 3. In this example, out of both surfaces 3_sa_ and 3_sb_ of the non-woven fabric 3, the one surface 3_sb_ is an approximately flat surface, whereas the other surface 3_sa_ has a wavy shape. Specifically, the surface 3_sa_ is made up of straight line-shaped groove portions 3_t_ and straight line-shaped projection portions 3_p_ that are formed alternatingly. The projection portions 3_p_ are formed by applying a known air stream blowing process (see JP 2009-11179A, for example) such that fibers that were originally in the groove portion 3_t_ regions are laterally blown together so as to pile up, thus forming a sparse state with large gaps between fibers. Accordingly, the non-woven fabric 3 is bulky overall. Also, multiple through-holes 3_h_, 3_h_ . . . that penetrate in the thickness direction may be formed in the groove portions 3_t_, and these through-holes are provided in this example.

The average basis weight of the non-woven fabric 3 is 10 to 200 (g/m$^2$) for example, the average basis weight of the central portion in the projection portions 3_p_ is 15 to 250 (g/m$^2$) for example, and the average basis weight of the bottom portion in the groove portions 3_t_ is 3 to 150 (g/m$^2$) for example.

Also, it is favorable that the fibers of the non-woven fabric 3 are composite fibers having a core-in-sheath structure with a PET core and a PE sheath, but other thermoplastic resin fibers may be used. For example, composite fibers having a core-in-sheath structure with a PP core and a PE sheath may be used, fibers with a side-by-side structure, or single-component fibers made up solely of a thermoplastic resin may be used.

Furthermore, the non-woven fabric 3 may have crimped fibers. Note that crimped fibers are fibers having a crimped shape, such as a zigzag shape, an Ω shape, a spiral shape, or the like.

Also, the fiber length of the fibers included in the non-woven fabric 3 is selected from the range of 20 to 100 mm for example, and the fiber density is selected from the range of 1.1 to 8.8 (dtex) for example.

Figure 2:
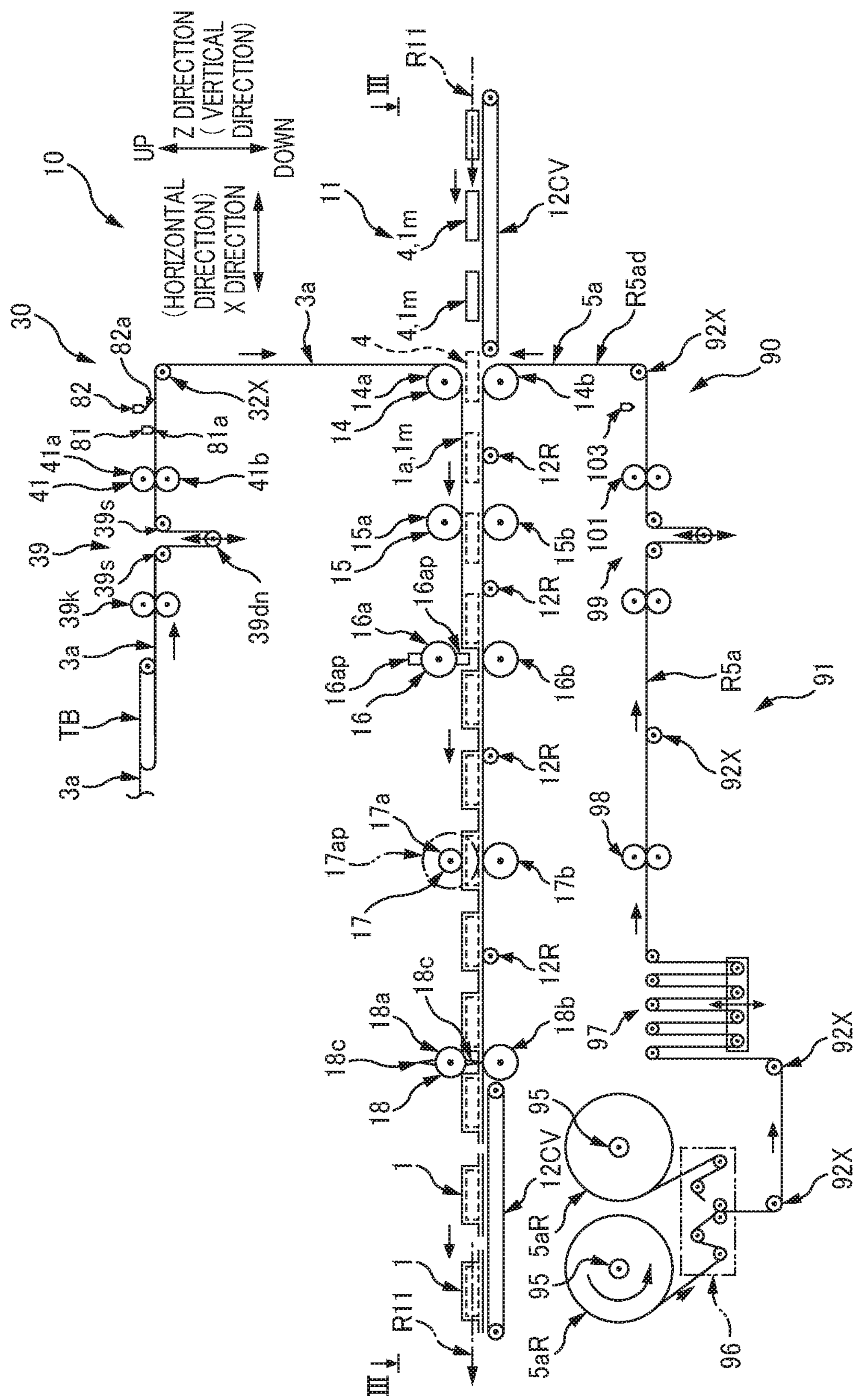
FIG. 2 is a schematic side view of a manufacturing line 10 for manufacturing the pet sheet 1.
Figure 3:
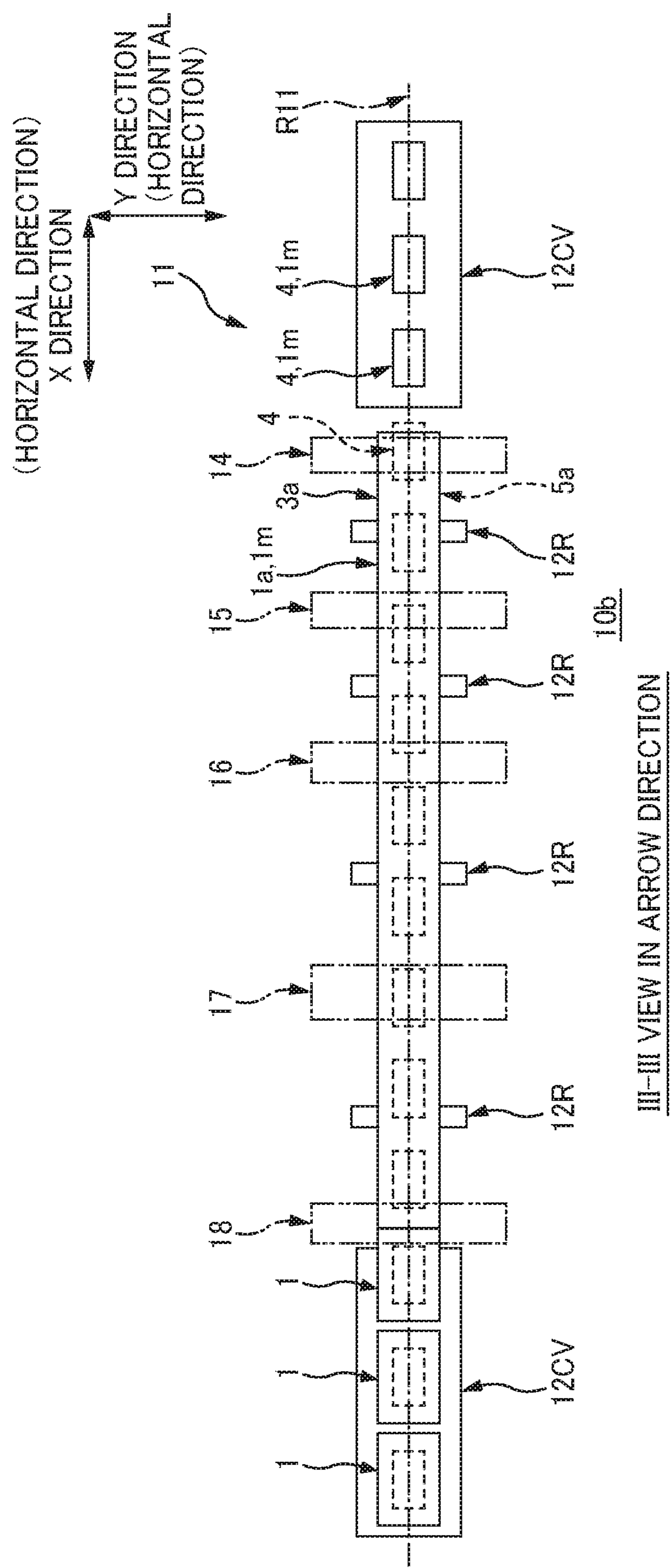
FIG. 3 is a view of a section III-III in FIG. 2 in the direction indicated by arrows.

FIG. 2 is a schematic side view of a manufacturing line 10 for manufacturing the pet sheet 1. FIG. 3 is a view of a section III-III in FIG. 2 in the direction indicated by arrows.

As shown in FIG. 2, the manufacturing line 10 for the pet sheet 1 has a main line 11 and sub lines 30 and 90. In the main line 11, basically, conveyance of the absorbent body 4, which is an intermediate product 1_m_ making up a primary part of the pet sheet 1, assembly of parts 3_a_ and 5_a_, which are supplied from the sub lines 30 and 90, to the absorbent body 4, and various processes for a continuous body 1_a_ of pet sheets 1, which is an intermediate product 1_m_ with a shape changed due to assembly, and the like are sequentially performed, and consequently the pet sheet 1 is finally manufactured.

In each of the sub lines 30 and 90, basically, a pre-treatment is applied to the corresponding part, that is to say the part 3_a_ or 5_a_. In this example, the parts 3_a_ and 5_a_ are respectively a continuous sheet 3_a_ of the top sheets 3 (simply referred to hereinafter as "the top sheet 3_a_") and a continuous sheet 5_a_ of the back sheets 5 (simply referred to hereinafter as "the back sheet 5_a_"), and the pre-treatment includes application of the hot-melt adhesive to the top sheet 3_a_ and the back sheet 5_a_, a bulk restoring process for the non-woven fabric 3_a_ serving as the material of the top sheet 3_a_, and the like, for example. For this reason, in this example, the sub line 30 for top sheets 3_a_ and the sub line 90 for back sheets 5_a_ are provided as the sub lines 30 and 90. The following provides a description of the main line 11, the sub line 30 for top sheets 3_a_, and the sub line 90 for back sheets 5_a_. In the following description, the three directions of the manufacturing line 10 that are orthogonal to one another are referred to as the X direction, the Y direction, and the Z direction. Here, the X direction and the Y direction are each oriented in the horizontal direction as shown in FIG. 3, whereas the Z direction is oriented in the vertical direction as shown in FIG. 2. Also, as shown in FIG. 3, the X direction and the Y direction are orthogonal to each other, the X direction corresponds to the "first direction" related to the claims, and the Y direction corresponds to the "second direction" related to the claims.

Main Line 11

As shown in FIG. 3, the main line 11 has a straight line-shaped conveying route R11 along the X direction in plan view. Specifically, when the main line 11 is viewed in the direction parallel to the vertical direction from above in the vertical direction, the main line 11 has the straight line-shaped conveying route R11 (corresponding to the first conveying route) along the X direction (corresponding to the first direction). The conveying route R11 is referred to hereinafter as "the main conveying route R11".

The main conveying route R11 is provided with appropriate conveying devices such as a conveyor 12CV and a conveying roller 12R in order to convey the intermediate products 1_m_ related to the pet sheet 1, such as the absorbent body 4 and the continuous body 1_a_ of pet sheets 1. The conveyor 12CV is basically configured with an endless belt that is driven to revolve and whose outer circumferential surface serves as the conveying surface. In some cases, however, the conveying surface may be additionally provided with a sucking function and the conveyor 12CV may be configured to convey the intermediate products 1_m_ while sucking them. Alternatively, two endless belts may be arranged above and below so as to face each other, and the conveyor 12CV may be configured to convey the intermediate products 1_m_ while clamping the intermediate products 1_m_ between the endless belts with some degree of pressure. The conveying roller 12R may be a driving roller that drives to rotate using rotation force obtained from an appropriate drive source such as a servo motor, or a driven roller that is driven to rotate by rotation force obtained by being brought into contact with the intermediate products 1_m_ to be conveyed.

Devices 14, 15, 16, 17, and 18 (corresponding to the processing devices) that belong to the main line 11, as well as the conveying devices 12CV and 12R, are arranged in the manufacturing line 10 and supported by an appropriate support member (not shown) provided for the manufacturing line 10. In this example, a so-called panel board (not shown) is used as an example of the support member. This panel board is a plate member erected vertically on a floor portion 10_b_ of the manufacturing line 10 and has a vertical surface (surface whose normal direction is oriented in the horizontal direction), and the devices 14, 15, and so on are supported on the vertical surface in a cantilevered state, for example. The normal direction of the vertical surface is orientated in the Y direction, and the Y direction in FIG. 2 is oriented in a direction penetrating the paper surface of FIG. 2. Note that the aforementioned support member is not limited in any way to being a panel board, and another support member may be used.

As shown in FIG. 2, multiple absorbent bodies 4, 4 . . . are conveyed to the main conveying route R11 in the X direction, which is the conveying direction, from an upstream process, with intervals in the conveying direction. In the example shown in FIG. 2, each of the absorbent bodies 4, 4 . . . in the main conveying route R11 is conveyed in the state where the position in the vertical direction, that is to say the Z direction, is maintained fixed. However, there is no limitation whatsoever to this. Specifically, the position in the Z direction (the vertical direction) of the absorbent bodies 4 may each be changed according to the position in the X direction.

To the main conveying route R11, the top sheet 3*a* (corresponding to the part) is input from the sub line 30 for top sheets 3*a*, at a predetermined position in the X direction, and the back sheet 5*a* is input from the sub line 90 for back sheets 5*a*, at the same predetermined position. A joining device 14 is arranged at this input position.

In this example, the joining device 14 has a pair of upper and lower rolls 14*a* and 14*b* that are driven to rotate about rotation shafts along the Y direction. The drive source of the pair of rolls 14*a* and 14*b* is a servo motor, for example. The pair of rolls 14*a* and 14*b* is rotated with the motor with their outer circumferential surfaces opposing each other, so as to carry out the absorbent bodies 4 downstream in the X direction. Rotation speed values V14*a* and V14*b* of the rolls 14*a* and 14*b* are subjected to cooperation control so as to be approximately the same value as a conveying velocity value V4 of the absorbent body 4 in the main conveying route R11.

As shown in FIG. 2, the top sheet 3*a* input from the sub line 30 for top sheets 3*a* is fed in between the pair of rolls 14*a* and 14*b* while being wound around the upper roll 14*a* of the pair of upper and lower rolls 14*a* and 14*b* of the joining device 14. Furthermore, the back sheet 5*a* input from the sub line 90 for back sheets 5*a* is fed in between the pair of rolls 14*a* and 14*b* while being wound around the lower roll 14*b* of the pair of upper and lower rolls 14*a* and 14*b*.

Thus, the three materials, namely the top sheet 3*a*, the absorbent body 4, and the back sheet 5*a*, pass together between the pair of rolls 14*a* and 14*b*, and are clamped with the pair of rolls 14*a* and 14*b* as they pass through, and thus the three materials 3*a*, 4, and 5*a* are joined. Consequently, the continuous body 1*a* of pet sheets 1, which is an intermediate product 1*m* with a shape changed from that of the absorbent body 4, is manufactured.

In the sub line 30 for top sheets 3*a* and the sub line 90 for back sheets 5*a*, the hot-melt adhesive is applied to the top sheet 3*a* and the back sheet 5*a* in order to subject them to the aforementioned joining. This application will be described later.

In the example shown in FIG. 2, in order to make the joining more reliable, three pressing devices 15, 16, and 17 (corresponding to processing devices) are provided in a position in the main conveying route R11 that is downstream of the joining device 14 in the X direction. The first pressing device 15 is a so-called light pressing device and very lightly presses approximately the entire surface of the continuous body 1*a* of pet sheets 1. The second pressing device 16 is a so-called end pressing device and selectively presses portions of the continuous body 1*a* of pet sheets 1 where the absorbent body 4 does not exist, that is to say the portions between adjacent absorbent bodies 4, 4 in the conveying direction. The last third pressing device 17 is a so-called side edge pressing device that selectively presses portions of the continuous body 1*a* of pet sheets 1 where the absorbent body 4 does not exist, that is to say the both end portions in the Y direction.

The inclusion of these three pressing devices 15, 16, and 17 makes it possible for the three members of the non-woven fabric 3*a*, the absorbent body 4, and the back sheet 5*a* to be joined with a higher adhesion strength.

A device having a pair of upper and lower rolls 15*a* and 15*b* that rotate with their smooth outer circumferential surfaces opposing each other can be given as an example of the light pressing device 15. Also, the following devices can be given as examples of the end pressing device 16 and the side edge pressing device 17. The end pressing device 16 has a pair of upper and lower rolls 16*a* and 16*b* that rotate with their outer circumferential surfaces opposing each other, and two projection portions 16*ap* that correspond to the portions between the absorbent bodies 4, 4 are provided on the outer circumferential surface of at least the roll 16*a* of the pair of rolls 16*a* and 16*b*. Also, the side edge pressing device 17 has a pair of rolls 17*a* and 17*b* that rotate with their outer circumferential surfaces opposing each other, a pair of ring-shaped projection portions 17*ap*, 17*ap* is respectively provided on the both end portions of the outer circumferential surface in the Y direction on at least the one roll 17*a* of the pair of upper and lower rolls 17*a* and 17*b*, and these projection portions 17*ap*, 17*ap* selectively press the portions of the continuous body 1*a* of pet sheets 1 where the absorbent body 4 does not exist, that is to say the both end portions in the Y direction.

As shown in FIG. 2, a rotary cutter device 18 is provided in a position on the downstream side of the side edge pressing device 17 in the main conveying route R11. The continuous body la of pet sheets 1 pressed with the side edge pressing device 17 passes through the rotary cutter device 18.

The rotary cutter device 18 (corresponding to a processing device) has a pair of upper and lower rolls 18*a* and 18*b*. The rolls 18*a* and 18*b* each rotate about a rotation shaft along the Y direction so as to feed the continuous body 1*a* of pet sheets 1 downstream in the X direction. The drive source of this rotation is a servo motor. The one roll 18*a* of the pair of upper and lower rolls 18*a* and 18*b* is a cutter blade roll 18*a* that has cutter blades 18*c* on the outer circumferential surface thereof, and the other roll 18*b* is an anvil roll 18*b* that receives the cutter blades 18*c* in the smooth outer circumferential surface thereof. When portions of the continuous body 1*a* of pet sheets 1 between absorbent bodies 4, 4 pass between these rolls 18*a* and 18*b*, the cutter blades 18*c* of the cutter blade roll 18*a* come into contact with the portions and consequently the continuous body 1*a* is cut, and thus pet sheets 1 are manufactured.

Sub Line 30 for Top Sheet 3*a*

Figure 4:
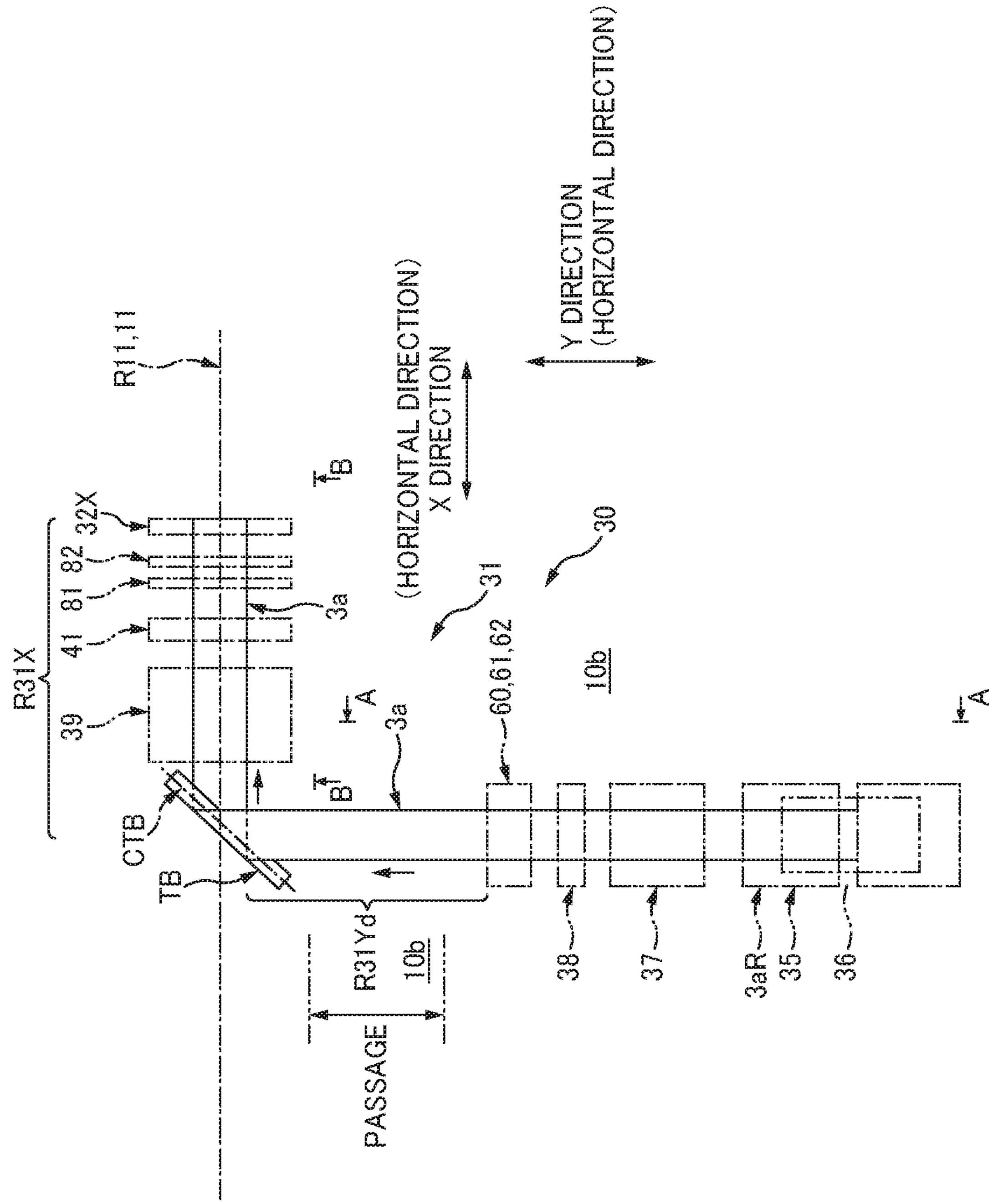
FIG. 4 is a schematic plan view of a sub line 30 for top sheets 3*a* viewed from above.
Figure 5:
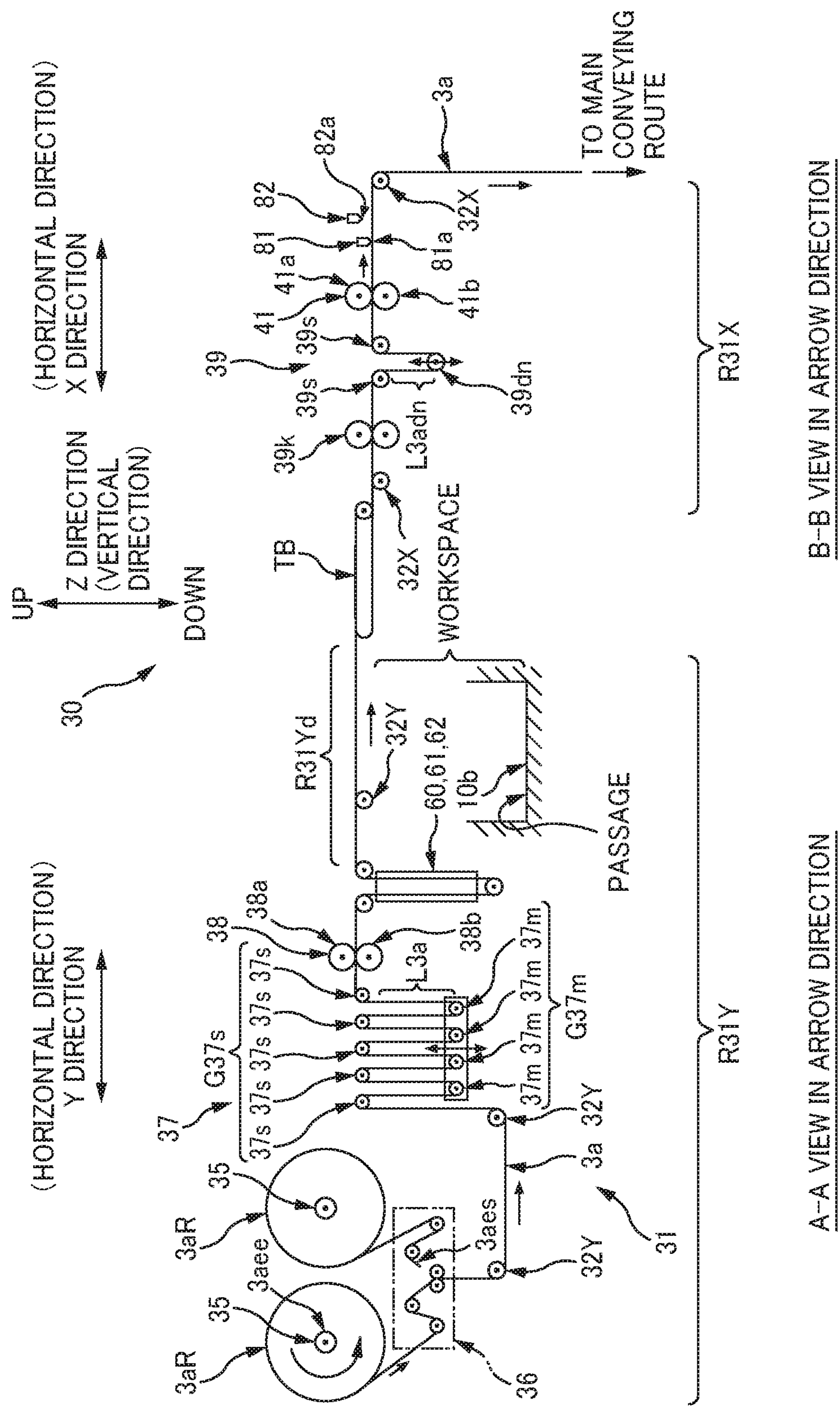
FIG. 5 is a schematic side view in which a view of a section A-A in FIG. 4 in the direction indicated by arrows and a view of a section B-B in FIG. 4 in the direction indicated by arrows are joined to each other.

FIG. 4 is a schematic plan view of the sub line 30 for top sheets 3*a* viewed from above, and FIG. 5 is a schematic side view in which a view of a section A-A in FIG. 4 in the direction indicated by arrows and a view of a section B-B in FIG. 4 in the direction indicated by arrows are joined to each other.

As shown in FIG. 4 and FIG. 5, the sub line 30 for top sheets 3*a* has: a conveying device 31 that feeds the non-woven fabric 3*a* serving as the material of the top sheet 3*a* from non-woven fabric whole cloths 3*a*R and conveys it to the aforementioned main conveying route R11; a bulk restoring device 60 that restores the bulk of the non-woven fabric 3*a* by heating the non-woven fabric 3*a* fed from the non-woven fabric whole cloth 3*a*R; and adhesive application devices 81 and 82 that apply the hot-melt adhesive for the aforementioned joining, to the non-woven fabric 3*a* with the restored bulk. Note that in the following description, the top sheet 3*a* is simply referred to as "the non-woven fabric 3*a*".

Here, as shown in FIG. 4, in plan view of the sub line 30, a heating unit 61 that makes up the main part of the bulk restoring device 60 is located in a position that is displaced from the main conveying route R11 of the main line 11 in the Y direction (corresponding to the second direction). That is to say, in plan view, the heating unit 61 is located in a position that does not overlap the main conveying route R11 of the aforementioned main line 11.

For this reason, the heat radiated from the heating unit 61 itself is effectively prevented from having a thermal influence on the intermediate products 1*m* in the main conveying route R11 and the devices 14, 15, 16, 17, and 18 in the route R11. That is to say, although the air that has been heated with the heat radiated with the heating unit 61 travels upward due to the reduced specific gravity thereof, the main conveying route R11 does not exist directly above the heating unit 61, as can be seen from FIG. 4. Thus, the heated air is effectively prevented from heating the intermediate products 1*m* and so on in the main conveying route R11.

Also, as described above, the heating unit 61 is located in a position that is displaced from the main conveying route R11 of the main line 11 in the Y direction. For this reason, before inputting the non-woven fabric 3*a* heated with the heating unit 61 to the main conveying route R11 of the aforementioned main line 11, it is possible to secure a conveying route R31Yd (corresponding to the second conveying route) to convey the non-woven fabric 3*a* at a high temperature in the Y direction, and it is thus possible to subject the non-woven fabric 3*a* at a high temperature to natural cooling while it passes through the conveying route R31Yd. As a result, it becomes possible to input the non-woven fabric 3*a* at a reduced temperature to the main conveying route R11, and accordingly the non-woven fabric 3*a* is effectively prevented from having a thermal influence on the intermediate products 1*m* and the devices 14, 15, and so on in the main conveying route R11.

Furthermore, it is likely that empty space remains in a position that is displaced from the main conveying route R11 in the Y direction in plan view. Thus, in the case of adding the bulk restoring device 60 to an existing manufacturing line 10 for example, it is easy to secure a space for installing the heating unit 61.

Incidentally, the description "the heating unit 61 of the bulk restoring device 60 is located in a position displaced from the main conveying route R11 in the Y direction" above means "the heating unit 61 is located in a position at which no portion of the heating unit 61 overlaps the main conveying route R11 in plan view, that is to say when viewed from above". Specifically, the description means "the heating unit 61 is located in a position at which no portion of the heating unit 61 overlaps the movement locus R11 of the intermediate products 1*m*".

The following provides a description of the constituent elements 31, 60, 81, and 82 of the sub line 30 for top sheets 3*a*.

(1) Conveying Device 31

As shown in FIG. 4, the conveying device 31 has two kinds of conveying routes R31X and R31Y as conveying routes for the non-woven fabric 3*a*. Specifically, the conveying device 31 has the Y direction conveying route R31Y for conveying the non-woven fabric 3*a* straight along the Y direction in plan view, and the X direction conveying route R31X for conveying the non-woven fabric 3*a* straight along the X direction in plan view, as the conveying routes. The Y direction conveying route R31Y is located on the upstream side of the X direction conveying route R31X in the conveying direction. Thus, the non-woven fabric 3*a* fed from the non-woven fabric whole cloths 3*a*R first passes through the Y direction conveying route R31Y. Then, the conveying direction of the non-woven fabric 3*a* is converted from the Y direction to the X direction at a 45°-turn bar TB arranged at the boundary between the Y direction conveying route R31Y and the X direction conveying route R31X, and consequently the non-woven fabric 3*a* enters the X direction conveying route R31X. Here, the X direction conveying route R31X in plan view overlaps the main conveying route R11 of the main line 11 along approximately the entire length of the X direction conveying route R31X. Thus, the non-woven fabric 3*a* passes through the X direction conveying route R31X, reaches a position directly above a joining device 41 in the main conveying route R11 (FIG. 2), and at the position, the non-woven fabric 3*a* swiftly enters the main conveying route R11 from above the main conveying route R11.

Incidentally, the 45°-turn bar TB is a cylindrical rod-shaped member having a smooth outer circumferential surface, for example, and has been generated from a burnished rod made of metal such as stainless steel, a round rod whose outer circumferential surface has an improved slipperiness due to surface treatment, or the like. As shown in FIG. 4, the direction of a central shaft CTB of the turn bar TB that passes through the center of circle, which is the center of the cross section, is oriented in the direction between the X direction and the Y direction in the horizontal plane. Thus, the non-woven fabric 3*a* is wound around the outer circumferential surface of the turn bar TB, the non-woven fabric 3*a* slides along the outer circumferential surface, and thus the conveying direction of the non-woven fabric 3*a* is swiftly converted from the Y direction to the X direction.

As shown in FIG. 5, the two kinds of conveying routes R31X and R31Y are respectively formed with multiple conveying rollers 32X, 32X . . . and multiple conveying rollers 32Y, 32Y . . . The Y direction conveying rollers 32Y with which the Y direction conveying route R31Y is formed are supported so as to be rotatable about rotation shafts along the X direction, and thus the non-woven fabric 3*a* is conveyed in the Y direction with the width direction thereof being oriented in the X direction. On the other hand, the X direction conveying rollers 32X with which the X direction conveying route R31X is formed are supported so as to be rotatable about rotation shafts along the Y direction, and thus the non-woven fabric 3*a* is conveyed in the X direction with the width direction thereof being oriented in the Y direction.

As shown in FIG. 4 and FIG. 5, the Y direction conveying route R31Y has feeding devices 35, 35, a material joining device 36, an accumulator device 37, and an upstream pinch roll device 38, lined up in the stated order from upstream to downstream in the conveying direction. The X direction conveying route R31X has a tension control device 39 and a downstream pinch roll device 41 lined up in the stated order from upstream to downstream in the conveying direction. Note that the adhesive application devices 81 and 82 are provided in positions on the downstream side of the downstream pinch roll device 41 in the X direction conveying route R31X, to apply an adhesive to the non-woven fabric 3*a*.

The devices 39 and 41 belonging to the X direction conveying route R31X, as well as the aforementioned X direction conveying rollers 32X, 32X, are supported with the aforementioned panel board that supports the devices 14, 15, and so on in the main conveying route R11. On the other hand, the devices 35, 35, 36, 37, and 38 belonging to the Y direction conveying route R31Y, as well as the aforementioned Y direction conveying rollers 32Y, 32Y . . . are supported with a support member that is different from the aforementioned panel board in the main conveying route R11. The support member (not shown) is a panel board that is arranged along the Y direction on the floor portion 10*b* of the manufacturing line 10, for example, and has a vertical surface whose normal direction is oriented in the X direction. The devices 35, 35, 36, 37, and 38 belonging to the Y direction conveying route R31Y are supported on the vertical surface in a cantilevered state, for example.

As shown in FIG. 5, the feeding devices 35 are devices that form the starting end of the Y direction conveying route R31Y, and specifically, each of the feeding devices 35 feeds the non-woven fabric 3*a* from the non-woven fabric whole cloths 3*a*R, along the Y direction conveying route R31Y. For this reason, the feeding devices 35 have rotation shafts along the X direction, and support the non-woven fabric whole cloths 3*a*R such that the non-woven fabric whole cloths 3*a*R are rotatable about the rotation shafts. The rotation shafts are driven to rotate with a servomotor (not shown) that serves as a drive source, for example, and thus the non-woven fabric 3*a* is fed from the non-woven fabric whole cloths 3*a*R. Note that the servo motor performs the feeding operation in coordination with the accumulator device 37. This coordination will be described later.

In this example of a plurality of devices, two feeding devices 35, 35 are provided. Basically, they are switched between each other and used alternatingly. Specifically, in this configuration, while one of the feeding devices 35 is feeding the non-woven fabric 3*a*, the other feeding device 35 is in the standby state, and then when the non-woven fabric whole cloth 3*a*R of the one feeding device 35 runs out, the feeding device 35 in the standby state begins to feed the non-woven fabric 3*a*. Note that these feeding devices 35 are well known, and thus will not be described in detail.

The material joining device 36 is also a device provided in the Y direction conveying route R31Y. At a time somewhat before the operating feeding device 35 completes the feeding of all of the non-woven fabric 3*a* from the non-woven fabric whole cloth 3*a*R, the material joining device 36 joins a trailing end portion 3*aee* of the non-woven fabric 3*a* of that whole cloth 3*a*R to a leading end portion 3*aes* of the non-woven fabric 3*a* of the non-woven fabric whole cloth 3*a*R attached to the standby feeding device 35. Accordingly, it is possible to continuously feed the non-woven fabric 3*a* without interruption. Note that the material joining device 36 is also well known, and thus will not be described in detail.

The accumulator device 37 is also a device provided in the Y direction conveying route R31Y, and accumulates the non-woven fabric 3*a* fed from the feeding device 35 so as to be able to be dispensed downstream in the conveying direction. In the case where the non-woven fabric 3*a* is not fed from the feeding device 35, such as when joining processing is performed with the material joining device 36, the accumulator device 37 dispenses the non-woven fabric 3*a* accumulated therein downstream, thus preventing downstream processing from being influenced by the pause in feeding from the feeding device 35. Note that the non-woven fabric 3*a* is fed from the feeding device 35 with a faster velocity value (m/min) than the conveying velocity value (m/min) of the non-woven fabric 3*a* in a position immediately downstream of the accumulator device 37, from when the pause in feeding from the feeding device 35 ends until when a specified accumulation amount is reached, and thus the accumulator device 37 accumulates an amount of the non-woven fabric 3*a* equal to the amount that was dispensed during the pause in feeding.

In this example, the accumulator device 37 has a fixed roller group G37*s* made up of multiple rollers 37*s*, 37*s* . . . that are fixed at fixed positions, and a movable roller group G37*m* made up of multiple rollers 37*m*, 37*m* . . . provided so as to be capable of moving back and forth in the vertical direction. The non-woven fabric 3*a* is alternatingly wound around the rollers 37*s* that belong to the fixed roller group G37*s* and the rollers 37*m* that belong to the movable roller group G37*m*, thus forming loops L3*a* in the non-woven fabric 3*a* and accumulating the non-woven fabric 3*a*.

Here, the movable roller group G37*m* moves back and forth in the vertical direction in accordance with the magnitude of tension (N) in the non-woven fabric 3*a*. Specifically, in the case where the magnitude of the tension in the non-woven fabric 3*a* is larger than a tension setting value (N) that has been set in advance, the movable roller group G37*m* moves such that the loops L3*a* decrease in size, and thus the accumulated non-woven fabric 3*a* is dispensed and supplied downstream. In the case where the magnitude of the tension in the non-woven fabric 3*a* is smaller than the setting value, however, the movable roller group G37*m* moves such that the loops L3*a* increase in size, thus accumulating the non-woven fabric 3*a*. Accordingly, in a position immediately downstream from the accumulator device 37, the magnitude of the tension in the non-woven fabric 3*a* is substantially maintained at the setting value, and in this sense, the accumulator device 37 also exhibits a function similar to that of the later-described tension control device 39. Note that the accumulator device 37 is also well known, and thus will not be described in further detail.

The upstream pinch roll device 38 is also a device provided in the Y direction conveying route R31Y, and feeds the non-woven fabric 3*a* to the heating unit 61 of the bulk restoring device 60. Specifically, it has a pair of rolls 38*a* and 38*b* arranged such that their outer circumferential surfaces oppose each other, and at least either the roll 38*a* or the roll 38*b* is a driving roll 38*a* (38*b*) that is driven to rotate with a servo motor (not shown) that serves as a drive source. The non-woven fabric 3*a* is fed to the heating unit 61 with this driving rotation.

The driving roll 38*a* (38*b*) is driven to rotate in coordination with a driving roll 39*k* of the tension control device 39 located on the downstream side of the heating unit 61 in the conveying direction. For example, the driving roll 38*a* (38*b*) of the pinch roll device 38 is driven to rotate so as to maintain a constant ratio R between a rotation speed value V39k of the driving roll 39*k* of the tension control device 39 and a rotation speed value V38a (V38b) of the driving roll 38*a* (38*b*) of the pinch roll device 38. The ratio R (=V39k/V38a) is set to any value from 0.9 to 1.1, for example.

The tension control device 39 is a device provided in the X direction conveying route R31X, and is arranged on the downstream side of the heating unit 61 in the conveying direction. Also, the tension control device 39 adjusts the tension such that the magnitude of the tension (N) in the non-woven fabric 3*a* in a position immediately downstream of the device 39 is a predetermined target value (N).

The tension control device 39 is configured using a so-called dancer roll 39*dn*. Specifically, the tension control device 39 has a pair of fixed rolls 39*s*, 39*s* that are fixed at fixed positions with a gap between each other in the conveying direction, the dancer roll 39*dn* that is provided in a position between the pair of fixed rolls 39*s*, 39*s* and is provided so as to be capable of moving back and forth in the vertical direction, and a driving roll 39*k* that is provided on the upstream side of the dancer roll 39*dn* in the conveying direction. The non-woven fabric 3*a* is wound around all three of the pair of fixed rolls 39*s*, 39*s*, the dancer roll 39*dn,* and the driving roll 39*k*, and a loop L3*adn* is formed in the non-woven fabric 3*a* wound around the pair of fixed rolls 39*s*, 39*s* and the dancer roll 39*dn*. Force corresponding to twice the target value of the tension in the non-woven fabric 3*a* is applied to the dancer roll 39*dn* in the direction for increasing the size of the loop L3*adn* of the back and forth moving directions. Accordingly, in the case where the magnitude of the tension in the non-woven fabric 3*a* is larger than the target value, the dancer roll 39*dn* moves such that the loop L3*adn* decreases in size, whereas in the case where the magnitude of the tension in the non-woven fabric 3*a* is smaller than the target value, the dancer roll 39*dn* moves such that the loop L3*adn* increases in size. Meanwhile, the driving roll 39*k* is driven to rotate with a servo motor (not shown), and this motor rotates the driving roll 39*k* and feeds the non-woven fabric 3*a* such that the size of the loop L3*adn* is a predetermined value. For example, in the case where the size of the loop is larger than the predetermined value, the rotation speed value (m/min) of the driving roll 39*k* is reduced, whereas in the case where the size is smaller than the predetermined value, the rotation speed value of the driving roll 39*k* is increased. Accordingly, the magnitude of the tension in the non-woven fabric 3*a* in a position immediately downstream of the tension control device 39 is adjusted so as to be the target value.

The downstream pinch roll device 41 is also a device provided in the X direction conveying route R31X, and feeds the non-woven fabric 3*a* to the joining device 14 in the main line 11. Specifically, it has a pair of rolls 41*a* and 41*b* arranged such that their outer circumferential surfaces oppose each other, and at least either the roll 41*a* or the roll 41*b* is a driving roll 41*a* (41*b*) that is driven to rotate with a servo motor (not shown) that serves as a drive source. The non-woven fabric 3*a* is fed to the joining device 14 in the main conveying route R11 of the main line 11 by this driving rotation (FIG. 2). The driving roll 41*a* (41*b*) is driven to rotate in coordination with the joining device 14. For example, the driving roll 41*a* (41*b*) of the downstream pinch roll device 41 is driven to rotate such that the rotation speed value of rolls 14*a* and 14*b* included in the joining device 14 and the rotation speed value of the driving roll 41*a* (41*b*) of the downstream pinch roll device 41 are approximately the same value.

(2) Bulk Restoring Device 60

Figure 6A:
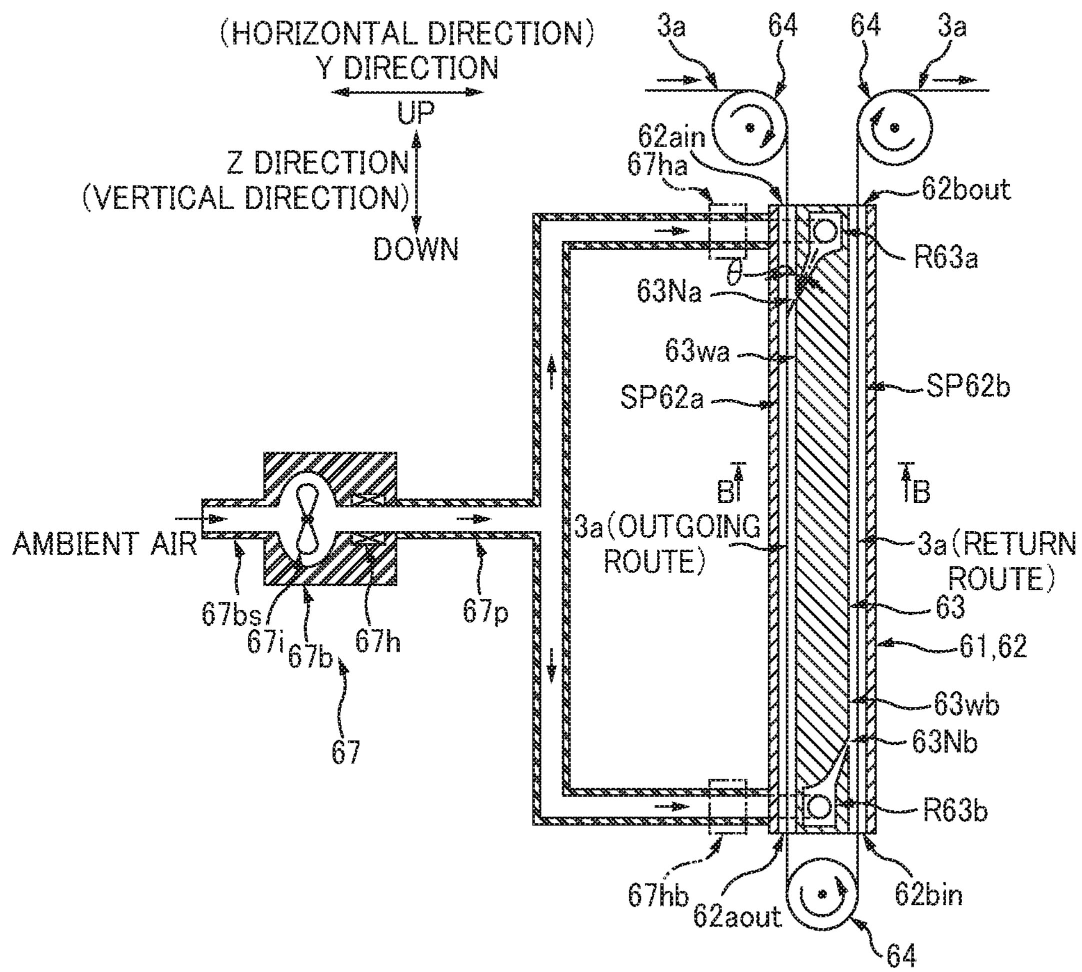
FIG. 6A is a schematic side view of a bulk restoring device 60.
Figure 6B:
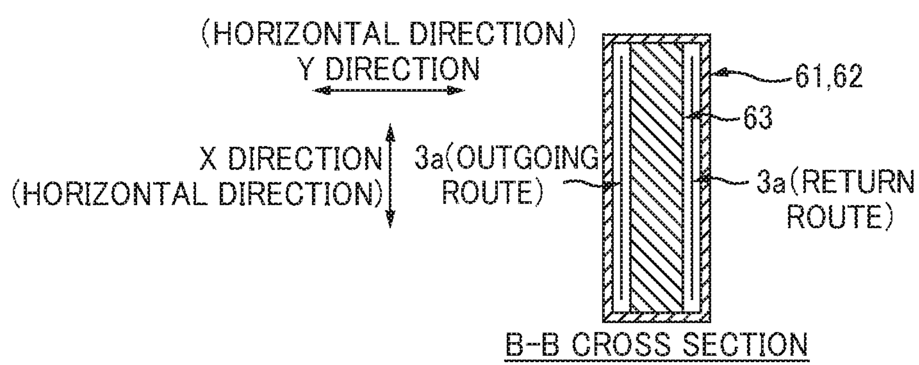
FIG. 6B is a cross sectional view of a section B-B in FIG. 6A.

FIG. 6A is a schematic side view of the bulk restoring device 60, and FIG. 6B is a cross sectional view of a section B-B in FIG. 6A. Note that the heating unit 61 making up a primary portion of the bulk restoring device 60 is shown in a cross-sectional view in FIG. 6A.

As shown in FIG. 6A, the bulk restoring device 60 has the heating unit 61 that heats the non-woven fabric 3*a* by blowing hot air onto the non-woven fabric 3*a* while passing it through the interior, and a hot air supplying device 67 that supplies hot air to the heating unit 61. As described above, the heating unit 61 is provided in the Y direction conveying route R31Y, and thus the heating unit 61 is arranged displaced in the Y direction from the main conveying route R11 in plan view (FIG. 4). Thus, the heat radiated from the heating unit 61 itself is effectively prevented from having a thermal influence on the intermediate products 1*m* and so on in the main conveying route R11. Also, it is easy to secure the conveying route R31Yd of the non-woven fabric 3*a* heated with the heating unit 61 along the Y direction. Accordingly, it is easy to swiftly subject the non-woven fabric 3*a* to natural cooling (FIG. 4).

Note that the route length of the conveying route R31Yd in FIG. 4 is determined by performing actual experiments, thermal analysis, or the like. For example, the route length of the conveying route R31Y is determined based on actual experiments or thermal analysis such that the temperature of the non-woven fabric 3*a* when the non-woven fabric 3*a* passes through the devices 14, 15, 16, 17, and 18 in the main conveying route R11 are lower than the upper limit value of the permissible temperatures of the devices 14, 15, 16, 17, and 18, and the temperature of the non-woven fabric 3*a* when the non-woven fabric 3*a* is joined to an intermediate product 1*m* (an absorbent body 4 in this example) is lower than the upper limit value of the permissible temperature of the intermediate products 1*m*. Here, supposing that the straight line-shaped conveying route R31Yd does not have a sufficient route length for cooling, the following configuration may be adopted. Specifically, the multiple Y direction conveying rollers 32Y, 32Y . . . may be alternatingly arranged in different positions in the vertical direction along the conveying route R31Yd, and multiple loops may be formed by winding the non-woven fabric 3*a* around each of the multiple Y direction conveying rollers 32Y, 32Y . . . in a zigzag shape to thus secure the route length of the conveying route R31Yd.

As shown in FIG. 6A and FIG. 6B, the heating unit 61 has a case member 62 that is open at the both end portions in the lengthwise direction, and multiple guide rollers 64, 64, 64 that are provided outside the case member 62 and guide the non-woven fabric 3*a* so as to move back and forth inside the case member 62. A straight outgoing path and return path in the conveying route for the non-woven fabric 3*a* are formed inside the case member 62 with the guide rollers 64, 64, 64.

Also, as shown in FIG. 6A, the case member 62 has a partition member 63 inside, and the partition member 63 divides the space inside the case member 62 into an outgoing route space SP62*a* and a return route space SP62*b*. Specifically, the outgoing route space SP62*a* and the return route space SP62*b* are separated such that air cannot travel therebetween. Also, due to the separation with the partition member 63, both an outgoing route entrance 62*ain* and a return route exit 62*bout* for the non-woven fabric 3*a* are formed in one of the both end portions of the case member 62 in the lengthwise direction, and both an outgoing route exit 62*aout* and a return route entrance 62*bin* for the non-woven fabric 3*a* are formed in the other end portion.

Furthermore, of both wall surfaces 63*wa* and 63*wb* of the partition member 63, the wall surface 63*wa* adjacent to the outgoing route space SP62*a* (also referred to hereinafter as the outgoing route wall surface 63*wa*), and of the both wall surfaces 636*wa* and 63*wb* of the partition member 63, the wall surface 63*wb* adjacent to the return route space SP62*b* (also referred to hereinafter as the return route wall surface 63*wb*) are each provided parallel to the conveying direction and the X direction, and thus the outgoing route wall surface 63*wa* and the return route wall surface 63*wb* are each approximately parallel to the surfaces of the non-woven fabric 3*a*. Also, a blast opening 63Na shaped as a slit elongated in the X direction is provided in a portion of the outgoing route wall surface 63*wa* on the upstream side in the outgoing route (corresponding to the "entrance-side portion of the case member"), and a blast opening 63Nb shaped as a slit elongated in the X direction is also provided in a portion of the return route wall surface 63*wb* on the upstream side in the return route (this corresponds to the "entrance-side portion of the case member").

More specifically, the partition member 63 has pressure chambers R63*a* and R63*b* inside in correspondence with the aforementioned portions. Hot air is supplied from the hot air supplying device 67 into the pressure chambers R63*a* and R63*b*. The pressure chambers R63*a* and R63*b* each have a cross-sectional shape (shape of the cross-section whose normal direction is the X direction) that is a tapered shape that roughly becomes increasingly narrow toward the downstream side in the conveying direction, and are respectively in communication with the corresponding outgoing route and return route spaces SP62*a* and SP62*b* at the tip portions of the tapered shape. Accordingly, the tip portions function as the blast openings 63Na and 63Nb. According to such blast openings 63Na and 63Nb, hot air is blasted toward one of both surfaces of the non-woven fabric 3*a*, while also being blasted toward the downstream side in the conveying direction with an acute angle of inclination θ relative to the surface of the non-woven fabric 3*a*.

Accordingly, the hot air blasted from the outgoing route blast opening 63Na comes into contact with the surface of the non-woven fabric 3*a* with a velocity component in a direction toward the downstream side in the conveying direction, continues to flow over the surface, and is then discharged to the outside through the exit 62*aout* (corresponding to the discharge port) located the most downstream in the conveying direction in the outgoing route space SP62*a*. Also, the hot air blasted from the return route blast opening 63Nb comes into contact with the surface of the non-woven fabric 3*a* with a velocity component in a direction toward the downstream side in the conveying direction, continues to flow over the surface, and is then discharged to the outside through the exit 62*bout* (corresponding to the discharge port) located the most downstream in the conveying direction in the return route space SP62*b*.

The hot air flows over the surface of the non-woven fabric 3*a* in this way, thus effectively avoiding a situation in which the hot air compresses the non-woven fabric 3*a* in the thickness direction of the non-woven fabric 3*a*, thereby making it possible to smoothly perform bulk restoration.

Also, by adjusting the hot air flow rate ($m^3$/min), a hot air velocity value Vw (m/min) can be set higher than the conveying velocity value V3 (m/min) of the non-woven fabric 3*a*. Accordingly, the hot air blasted from the blast openings 63Na and 63Nb passes over the non-woven fabric 3*a* in a manner of sliding over the surface of the non-woven fabric 3*a*, and is ultimately discharged to the outside through the exits 62*aout* and 62*bout*. Accordingly, the hot air can be reliably put in a turbulent state based on the relative velocity difference between the hot air and the non-woven fabric 3*a*. As a result, the heat transfer efficiency is dramatically improved, the non-woven fabric 3*a* can be efficiently heated, and the bulk is swiftly restored. Also, the fibers in the non-woven fabric 3*a* are randomly loosened by the hot air in a turbulent state, and the bulk restoration is promoted by this as well.

It should be noted that the wind velocity value Vw (m/min) of the hot air is a value obtained by the flow rate ($m^3$/min) of hot air supplied to the outgoing route space SP62*a* or the return route space SP62*b* being divided by the cross-sectional area of the outgoing route space SP62*a* or the return route space SP62*b* (i.e., the area of a cross-section whose normal direction is the conveying direction), for example.

Also, it is preferable that the magnitude relationship between the wind velocity value Vw and the conveying velocity value V3 described above holds true over the entire length of the outgoing route and return route spaces SP62*a* and SP62*b* in the conveying direction, but it is not necessarily required to hold true over the entire length. Specifically, as long as the magnitude relationship holds true in even a portion of the spaces SP62*a* and SP62*b*, the above-described actions and effects related to the turbulent state can be correspondingly obtained.

Note that the shapes of the outgoing route and return route blast openings 63Na and 63Nb are each a rectangle whose lengthwise direction is oriented in the X direction. Also, the X-direction dimension of the outgoing route blast opening 63Na is assumed to be the same value as the X-direction dimension of the outgoing route space SP62*a*, and the X-direction dimension of the return route blast opening 63Nb is assumed to be the same value as the X-direction dimension of the return route space SP62*b*, but there is no limitation whatsoever to this. For example, the blast openings 63Na and 63Nb may be smaller. Note that it is preferable that the X-direction dimension of the blast openings 63Na and 63Nb is larger than the width-direction dimension of the non-woven fabric 3*a* (X-direction dimension), and this configuration suppresses heating irregularity in the X direction.

Also, the widthwise-direction dimension of the blast openings 63Na and 63Nb (dimension in the direction orthogonal to the lengthwise direction) is selected and set to any value in the range of 1 mm to 10 mm, for example.

Furthermore, it is preferable that the angle θ that the hot air blast direction at the positions of the blast openings 63Na and 63Nb forms with the conveying direction of the non-woven fabric 3*a* falls within the range of 0° to 30°, and it is further preferable that this angle θ falls within the range of 0° to 10° (FIG. 6A). According to this configuration, it is possible to cause the hot air to reliably flow along the surface of the non-woven fabric 3*a*.

In the example in FIG. 6A, the heating unit 61 is of the vertical type in which the lengthwise direction of the case member 62 is oriented in the vertical direction, and thus the outgoing route and return route in the conveying route of the non-woven fabric 3*a* are vertical. Also, the route oriented in the direction from top to bottom is defined as the outgoing route and the route oriented in the direction from bottom to top (corresponding to the upward route) is defined as the return route. Thus, as shown in FIG. 5, it is possible to connect the Y direction conveying route R31Y to the X direction conveying route R31X with the height position of the Y direction conveying route R31Y in the vertical direction being high. As a result, it is possible to secure a workspace that serves as, for example, a passage for workers and construction vehicles, below the downstream end portion R31Yd of the Y direction conveying route R31Y. For example, as shown in FIG. 4 and FIG. 5, the aforementioned passage for workers and construction vehicles is set on the floor portion 10*b* of the manufacturing line 10. With the aforementioned configuration, the downstream end portion R31Yd of the Y direction conveying route R31Y can be set in a position that is sufficiently separated from the passage in the upward direction so as to be oriented along the Y direction. Thus, it is possible to prevent the Y direction conveying route R31Y from obstructing the passage.

Also, as shown in FIG. 6A, in the return route for conveying the non-woven fabric 3*a* upward, hot air is blasted upward from the blast opening 63Nb. With this hot air, the non-woven fabric 3*a* is conveyed due to the buoyancy of the hot air as if being blown upward. Thus, it is possible to reduce the upward tension that is to be applied to the non-woven fabric 3*a* in order to bring the non-woven fabric 3*a* upward. Consequently, it is possible to effectively suppress a reduction in the thickness-direction dimension of the non-woven fabric 3*a* due to the tension, that is to say a reduction in the bulk.

Furthermore, this vertical type is superior in that only a small amount of planar space is required for the installation of the heating unit 61.

However, the heating unit 61 is not limited in any way to being the vertical type, and may be of the horizontal type. Specifically, the lengthwise direction of the case member 62 may be oriented in the horizontal direction so that the outgoing route and the return route related to the conveying route of the non-woven fabric 3*a* are oriented along the horizontal direction. Furthermore, depending on the layout circumstances, the heating unit 61 may be arranged with the lengthwise direction of the case member 62 inclined relative to both the vertical direction and the horizontal direction.

As shown in FIG. 6A, the hot air supplying device 67 has a blower 67*b* and a heater 67*h*. The wind generated with the blower 67*b* is heated with the heater 67*h* to generate hot air, and this hot air is supplied to the pressure chambers R63*a* and R63*b* of the partition member 63 in the case member 62 of the heating unit 61 via an appropriate pipe member 67*p*. The hot air then travels through the pressure chambers R63*a* and R63*b* and is blasted through the blast openings 63Na and 63Nb.

The blower 67*b* has an impeller 67*i* that rotates using a motor, for example, as a drive source, and an inverter (not shown) that adjusts the rotation speed (rpm) of the motor. Accordingly, it is possible to perform VVVF inverter control, thus making it possible to adjust the flow rate ($m^3$/min) to any value via a change in the rotation speed (rpm) of the impeller 67*i*.

Also, the heater is an electric heater that performs heating using electricity (kW) for example, and the temperature of the hot air can be adjusted to any value by a change in the electricity input amount. Note that regarding the temperature of the hot air, it is sufficient that the temperature at the positions of the blast openings 63Na and 63Nb is greater than or equal to a temperature that is 50° C. lower than the melting point of the thermoplastic resin fibers included in the non-woven fabric 3*a*, and also less than the melting point. Setting the temperature in this range makes it possible to reliably restore the bulk while also preventing melting of the thermoplastic resin fibers.

As shown in FIG. 6A, the heater 67*h* may be built into the blower 67*b* or may be provided outside the blower 67*b*. In the case of providing the heater 67*h* on the outside, it is sufficient that heaters 67*ha* and 67*hb* are arranged in the vicinity of the case member 62 of the heating unit 61 as shown by virtual dashed double-dotted lines in FIG. 6A, and this configuration makes it possible to increase the response when adjusting the hot air temperature. Also, in this case, it is further preferable that the heaters 67*ha* and 67*hb* are provided for the blast openings 63Na and 63Nb. In other words, it is sufficient that the heater 67*ha* is provided in correspondence with the outgoing route blast opening 63Na, and the heater 67*hb* is separately provided in correspondence with the return route blast opening 63Nb. According to this configuration, it is possible to individually adjust the hot air temperature for the blast openings 63Na and 63Nb, thus making it possible to perform bulk restoration processing with more precise condition settings.

Note that the heaters 67*h*, 67*ha*, and 67*hb* are not limited in any way to being electric heaters, and any type of heater can be applied as long as it can heat a gas such as air that forms wind.

Also, although "wind" refers to a flow of air in this example, besides a flow of air, it broadly encompasses a flow of a gas such as nitrogen gas or an inert gas. In other words, nitrogen gas or the like may be blown out from the blast openings 63Na and 63Nb.

Incidentally, it is preferable that the hot air supplying device 67 is also arranged in a position that is displaced from the main conveying route R11 in the Y direction, and such an arrangement effectively prevents the hot air supplying device 67 from having a thermal influence on the intermediate products 1*m* or the like in the main conveying route R11 by heating the environmental air.

(3) Adhesive Application Devices 81 and 82

In the example in FIG. 2 and FIG. 5, two types of adhesive application devices 81 and 82 are provided in order to apply the hot-melt adhesive to the non-woven fabric 3*a*. Both the application devices 81 and 82 are provided in the X direction conveying route R31X. More specifically, the application devices 81 and 82 are configured to apply the adhesive to the non-woven fabric 3*a* in a position between a position on the downstream side of the heating unit 61 in the conveying direction and the position of the joining device 14 of the main line 11.

The application devices 81 and 82 respectively have discharge portions 81*a* and 82*a* for discharging the adhesive, as well as a pump (not shown). The pumps feed the hot-melt adhesive to the discharge portions 81*a* and 82*a* in a fluid state, and thus the fluid adhesive is discharged from the discharge portions 81*a* and 82*a*.

Here, the one application device 81 out of the two types is a contact application device, and the other application device 82 is a contactless application device. The contact application device 81 applies the adhesive with the discharge portion 81*a* in contact with or in the vicinity of the application target, whereas the contactless application device 82 applies the adhesive by dripping it from the discharge portion 82*a* that is sufficiently separated from the application target.

In the example in FIG. 5, firstly the contact application device 81 applies the adhesive to the non-woven fabric 3*a*, and thereafter the contactless application device 82 applies the adhesive at a downstream position.

The contact application device 81 applies the adhesive in a solid-coating application pattern in which the application target portions are the portions of the one surface of the non-woven fabric 3*a* that do not cover the absorbent bodies 4, 4 that is to say the portions of the one surface of the non-woven fabric 3*a* that are to be joined to the back sheet 5*a*. For this reason, the application device 81 has a slit-shaped nozzle elongated in the Y direction as the discharge portion 81*a*, and thus, whereas the adhesive is applied to the non-woven fabric 3*a* over approximately the entire length in the Y direction, the adhesive is discharged intermittently in the conveying direction such that the adhesive is selectively applied to only the aforementioned application target portions.

On the other hand, the contactless application device 82 applies the adhesive in a predetermined application pattern in which approximately the entirety of one surface of the non-woven fabric 3*a* is the application target portion. Here, this application pattern is a pattern in which multiple linear portions that are continuous in the conveying direction are lined up in the Y direction, and examples of the shapes of these linear portions include such as a straight line along the conveying direction, a spiral line along the conveying direction, and a wavy line along the conveying direction. In order to perform application in this application pattern, the application device 82 has multiple approximately circular hole-shaped nozzles lined up in the Y direction as the discharge portion 82*a*, and the adhesive is applied to approximately the entirety of the one surface of the non-woven fabric 3*a* in this application pattern by continuously dripping the adhesive from each of the nozzles.

Sub Line 90 for Back Sheets 5*a*

As shown in FIG. 2, the sub line 90 for back sheets 5*a* is provided directly below the main conveying route R11 of the main line 11. Consequently, the back sheet 5*a* is input to the main conveying route R11 from below the main conveying route R11 of the main line 11.

The sub line 90 for back sheets 5*a* has: a conveying device 91 that feeds the film material 5*a* serving as the material of the back sheet 5*a* from film material whole cloths 5*a*R and conveys the film material 5*a* to the aforementioned main conveying route R11; and an adhesive application device 103 that applies the hot-melt adhesive for the aforementioned joining with the joining device 14, to the film material 5*a* fed from the film material whole cloths 5*a*R.

The conveying device 91 has multiple conveying rollers 92X, 92X . . . that form the conveying route R5*a* for back sheets 5*a*, two feeding devices 95, a material joining device 96, an accumulator device 97, an upstream pinch roll device 98, a tension control device 99, and a downstream pinch roll device 101. The configurations of the devices 95, 95, 96, 97, 98, 99, and 101 are approximately the same as the devices 35, 35, 36, 37, 38, 39, and 41 for the above-described sub line 30 for top sheets 3*a*. Also, the configuration of the adhesive application device 103 is approximately the same as the aforementioned contactless application device 82. Thus, the description thereof is omitted.

In this example in FIG. 2, the conveying route R5*a* for back sheets 5*a* has a straight line shape along the X direction in plan view, and the conveying route R5*a* also overlaps the main conveying route R11 along approximately the entire length thereof in plan view. Thus, it is possible to swiftly input the back sheets 5*a* to the main conveying route R11 by merely orienting the conveying direction of the back sheets 5*a*, which are the film materials 5*a*, in the upward direction, in the downstream end portion R5*ad* of the conveying route R5*a*, as shown in FIG. 2.

The conveying route R5*a* of the sub line 90 for back sheets 5*a*, however, is not limited in any way to the above. Specifically, as with the conveying route of the sub line 30 for top sheets 3*a* in FIG. 4, the conveying route R5*a* may have a Y direction conveying route and an X direction conveying route, and the Y direction conveying route and the X direction conveying route may be connected to each other with a conveying direction switching mechanism like the 45°-turn bar TB. In such a case, the Y direction conveying route may have the feeding devices 95, 95, the material joining device 96, the accumulator device 97, and the upstream pinch roll device 98, and the X direction conveying route may have the tension control device 99 and the downstream pinch roll device 101, for example.

The manufacturing line 10 according to the first embodiment has been described above. When newly installing the manufacturing line 10, it is possible to apply the bulk restoring process to the non-woven fabric 3*a* for top sheets 3*a* from the beginning of the operation in the manufacturing line 10 by installing the bulk restoring device 60 as well. Also, when installing the bulk restoring device 60, in the case where the heating unit 61 of the device 60 is arranged in the Y direction conveying route R31Y, it is possible to effectively prevent the heating unit 61 from having a thermal influence on the intermediate products 1*m* and the devices 14, 15, 16, 17, and 18 in the main conveying route R11 of the main line 11.

On the other hand, in the case of adding the bulk restoring device 60 to an existing manufacturing line 10 that does not have the bulk restoring device 60, it is possible to add the device 60 so as not to have a thermal influence on the intermediate products 1*m* and the devices 14, 15, and so on in the main conveying route R11 by modifying the manufacturing line 10 in the following manner.

First, note that the existing manufacturing line 10 already has all the components except the bulk restoring device 60 before the modification is made (FIG. 2).

Specifically, the main line 11 has all of the devices 14, 15, 16, 16, 17, 18, 12CV, 12R, and so on. The sub line 90 for back sheets 5*a* also has all of the devices 95, 95, 96, 97, 98, 99, 101, 92X, and so on. The sub line 30 for top sheets 3*a* has all of the devices 35, 35, 36, 37, 38, 39, 41, 32X, 32Y, and so on except the heating unit 61 and the hot air supplying device 67 related to the bulk restoring device 60. Specifically, as shown in FIG. 4 and FIG. 5, the sub line 30 has the multiple Y direction conveying rollers 32Y, 32Y . . . with which the Y direction conveying route R31Y is formed, and the multiple X direction conveying rollers 32X, 32X . . . with which the X direction conveying route R31X is formed. The Y direction conveying route R31Y is provided with the feeding devices 35, 35, the material joining device 36, the accumulator device 37, and the upstream pinch roll device 38, and the X direction conveying route R31X is provided with the tension control device 39 and the downstream pinch roll device 41.

At the time of modifying the unmodified existing manufacturing line 10, first, as shown in FIG. 4 and FIG. 5, the heating unit 61 is arranged in a position on the downstream side in the conveying direction of the upstream pinch roll device 38 in the Y direction conveying route R31Y. In the case where the heating unit 61 is arranged in the position, the heating unit 61 is in the state of being arranged in a position that is displaced from the main conveying route R11 of the main line 11 in the Y direction, and thus the heating unit 61 is prevented from having a thermal influence on the intermediate products 1*m* and so on in the main conveying route R11. Also, when making the modification, the hot air supplying device 67 is also arranged in a position that is displaced from the main conveying route R11 in the Y direction. By arranging the hot air supplying device 67 in the position, it is also possible to prevent the hot air supplying device 67 from having a thermal influence on the intermediate products 1*m* and so on in the main conveying route R11.

Second Embodiment

Figure 7:
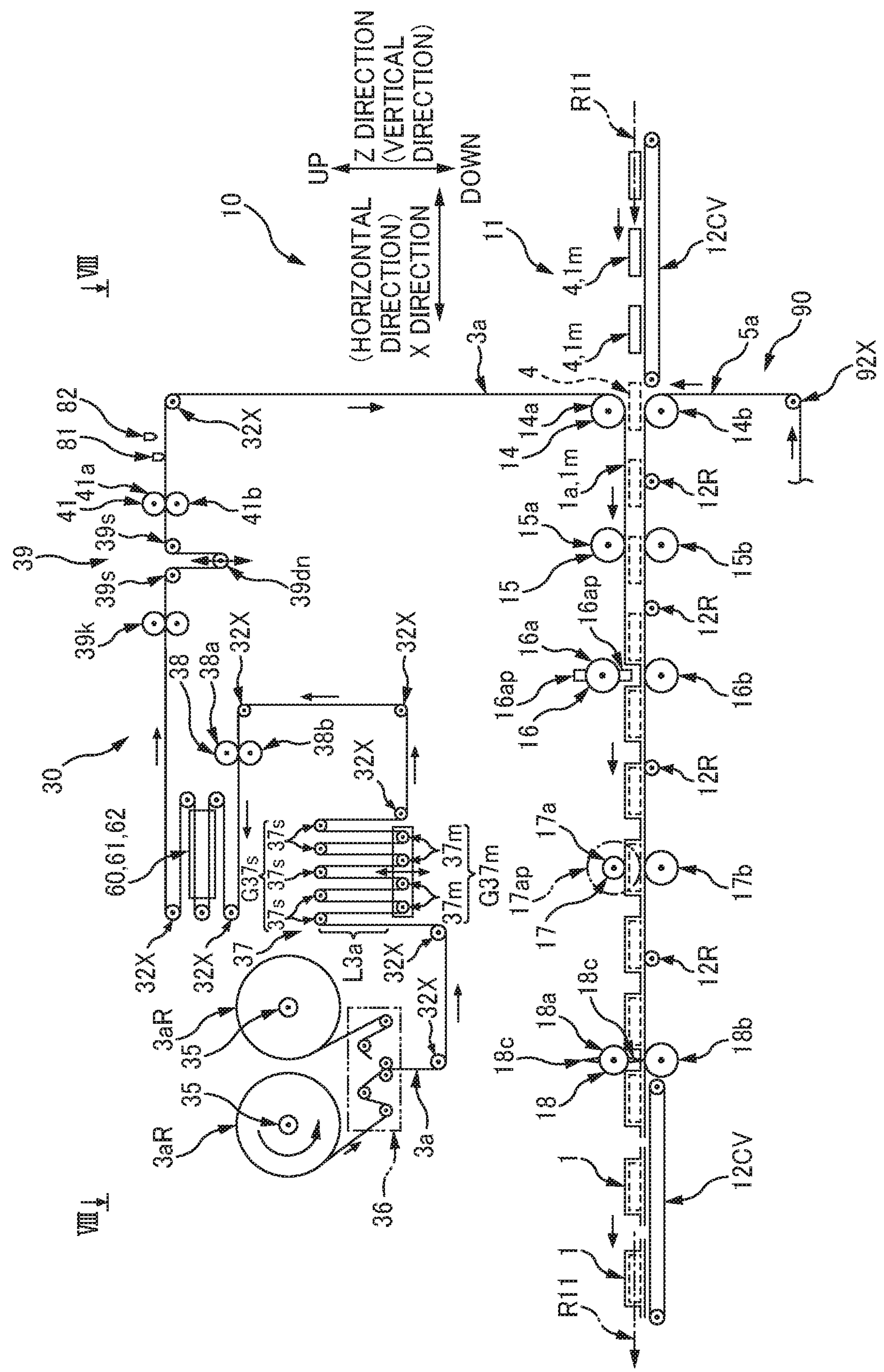
FIG. 7 is a schematic side view of a manufacturing line 10 according to a second embodiment.
Figure 8:
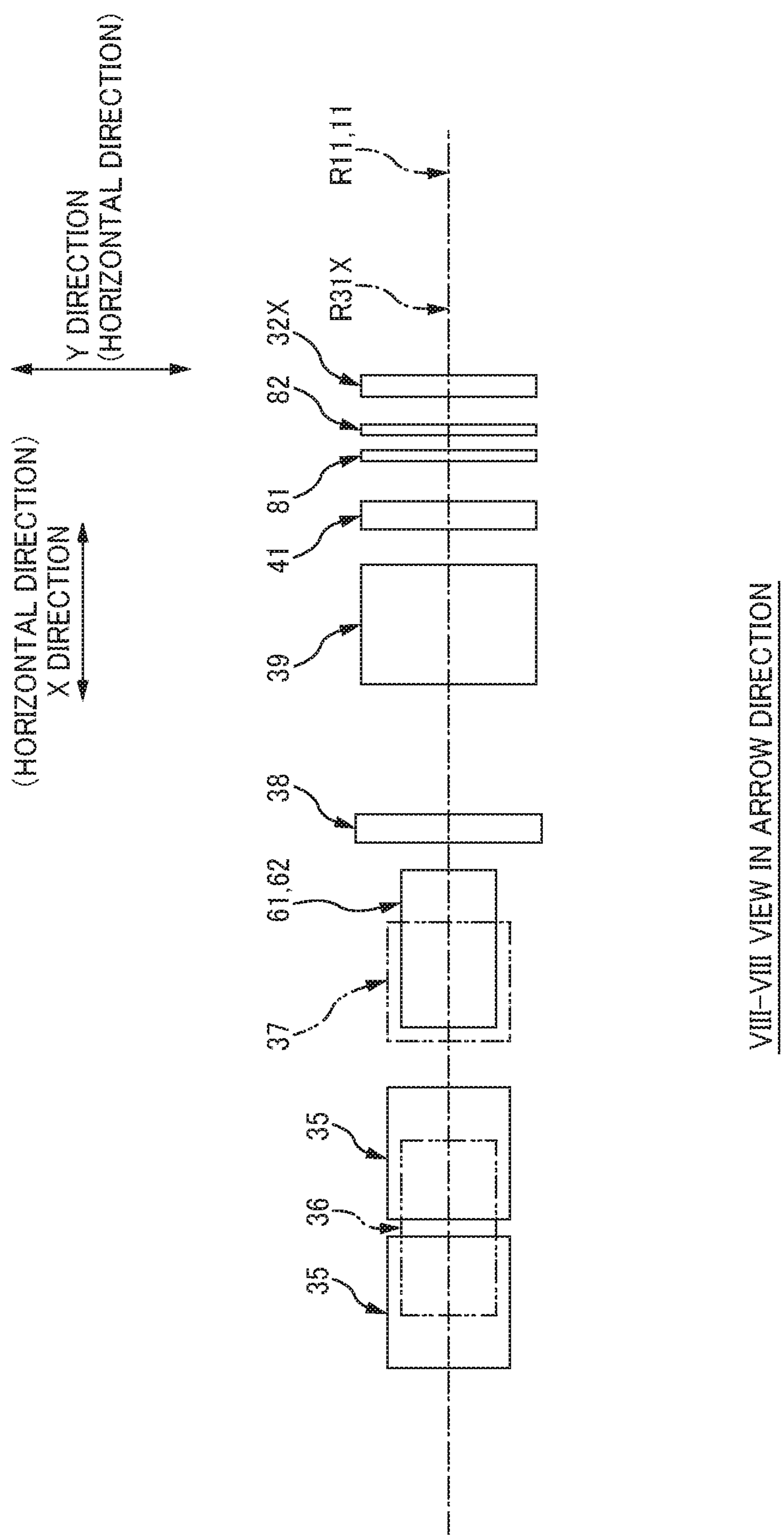
FIG. 8 is a view of a section VIII-VIII in FIG. 7 in the direction indicated by arrows.

FIG. 7 is a schematic side view of a manufacturing line 10 according to a second embodiment. FIG. 8 is a view of a section VIII-VIII in FIG. 7 in the direction indicated by arrows. In FIG. 8, the non-woven fabric 3*a* is not shown.

In the manufacturing line 10 according to the first embodiment above, in order to supress the thermal influence of the heating unit 61 of the bulk restoring device 60 on the intermediate products 1*m* and soon in the main line 11, the heating unit 61 is arranged in a position that is displaced from the main conveying route R11 of the main line 11 in the Y direction, as shown in FIG. 4. In this regard, in the second embodiment, as shown in FIG. 7 and FIG. 8, the same object is achieved by arranging the heating unit 61 directly above the main conveying route R11 of the main line 11. The details are as follows.

First, the air heated by the heat radiated with the heating unit 61 travels upward due to the reduced specific gravity thereof. In the second embodiment, the heating unit 61 is arranged above the main conveying route R11, and thus the main conveying route R11 does not exist directly above the heating unit 61. Thus, the heated air is effectively prevented from heating the intermediate products 1*m* and the devices 14, 15, and so on in the main conveying route R11, that is to say the heating unit 61 is effectively prevented from having a thermal influence.

Note that, in the second embodiment, as shown in FIG. 7, since the heating unit 61 is arranged directly above the main conveying route R11, the conveying route R31X of the sub line 30 for top sheets 3*a* is arranged directly above the main conveying route R11 along the entire length thereof. Specifically, in the second embodiment, the Y direction conveying route R31Y is omitted and only the X direction conveying route R31X is provided, and thus the X direction conveying route R31X is the only conveying route provided for the sub line 30 for top sheets 3*a*. Also, as described above, in plan view, the X direction conveying route R31X is set to have a straight line shape along the X direction, and the route R31X overlaps the main conveying route R11.

Such an X direction conveying route R31X is formed with the multiple X direction conveying rollers 32X, 32X . . . described above. Also, in the X direction conveying route R31X, the devices 35, 35, 36, 37, 38, 61, 39, 41, 81, and 82 are arranged in the following order from upstream to downstream in the conveying direction. That is, first, the two feeding devices 35, 35 that constitute the starting end of the conveying route R31X are arranged, and subsequently, the material joining device 36, the accumulator device 37, the upstream pinch roll device 38, the heating unit 61, the tension control device 39, and the downstream pinch roll device 41 are arranged in the stated order from upstream to downstream in the conveying direction. The non-woven fabric 3*a* successively passes through the devices 35, 35, 36, and so on in the stated order, and is then input to the main conveying route R11 of the main line 11.

Incidentally, the meaning of "directly above" in the above description "the heating unit 61 of the bulk restoring device 60 is arranged directly above the main conveying route R11" of course need only be interpreted in a general sense, but if a definition were presumed to be given, it would refer to an arrangement relationship in which in the case of being viewed in a plan view, that is to say in the case of being viewed from above, at least a part of the heating unit 61 appears to overlap the main conveying route R11 from above. More specifically, it would refer to an arrangement relationship in which at least part of the heating unit 61 appears to overlap the movement locus R11 of the intermediate products 1*m* from above.

In the second embodiment, although the heating unit 61 is arranged above the accumulator device 37 as shown in FIG. 7, the position at which the heating unit 61 is arranged is not limited in any way to this position. For example, the heating unit 61 may be arranged above the feeding devices 35, 35.

Also, in the example in FIG. 7, the heating unit 61 is of the horizontal type. Specifically, the heating unit 61 is arranged to be oriented such that the outgoing route and the return route of the conveying route for the non-woven fabric 3*a* each extends along the horizontal direction. Using the heating unit 61 of the horizontal type, it is possible to reduce the vertical dimension of the heating unit 61.

Accordingly, it is possible to effectively prevent problems that can occur due to the heating unit 61 being arranged directly above the main conveying route R11. For example, utility equipment such as a duct (not shown) is typically already arranged in the upper space within the building (not shown) for the manufacturing line 10. Supposing that the vertical dimension of the heating unit 61 is large, there is the risk of the heating unit 61, which is arranged directly above the main conveying route R11, interfering with the existing utility equipment, and accordingly it becomes difficult to house the heating unit 61 within the building.

In this regard, however, in the case of the horizontal type above, it is possible to reduce the vertical dimension of the heating unit 61, and thus it is possible to house the heating unit 61 within the building while effectively preventing the heating unit 61 from interfering with the utility equipment located above.

Mainly the differences from the first embodiment have been described above. The configurations of the devices 35, 35, 36, 37, 38, 61, 39, 41, 81, and 82 that belong to the sub line 30 for top sheets 3*a* are approximately the same as the configurations of those in the first embodiment. Also, the configuration of the main line 11 and the configuration of the sub line 90 for back sheets 5*a* are approximately the same as the configurations of those in the first embodiment. Thus, the description thereof is omitted.

When newly installing the manufacturing line 10 according to the second embodiment, it is possible to apply the bulk restoring process to the non-woven fabric 3*a* for top sheets 3*a* from the beginning of the operation in the manufacturing line 10 by installing the bulk restoring device 60 as well. In this regard, by arranging the heating unit 61 of the bulk restoring device 60 directly above the main conveying route R11 of the main line 11, it is possible to effectively prevent the heating unit 61 from having a thermal influence on the intermediate products 1*m* and the devices 14, 15, and so on in the main conveying route R11.

On the other hand, in the case of adding the bulk restoring device 60 to an existing manufacturing line 10 that does not have the bulk restoring device 60, it is possible to add the bulk restoring device 60 so as not to have a thermal influence on the intermediate products 1*m* and the devices 14, 15, and so on in the main conveying route R11 by modifying the manufacturing line 10 in the following manner.

First, as shown in FIG. 7, in the existing manufacturing line 10 at the time before the modification is made, the main line 11 already has all of the devices 14, 15, 16, 16, 17, 18, 12CV, 12R, and so on, and the sub line 90 for back sheets 5*a* already has all of the devices 95, 95, 96, 97, 98, 99, 101, 92X, and so on. The sub line 30 for top sheets 3*a* has all of the devices 35, 35, 36, 37, 38, 39, 41, 32X, 32Y, and so on except the heating unit 61 and the hot air supplying device 67 related to the bulk restoring device 60. Specifically, the sub line 30 has the X direction conveying route R31X in a position directly above the main conveying route R11 of the main line 11. In the X direction conveying route R31X, the feeding devices 35, 35, the material joining device 36, the accumulator device 37, the upstream pinch roll device 38, the tension control device 39, the downstream pinch roll device 41, and the adhesive application devices 81 and 82 are arranged.

At the time of modifying the unmodified existing manufacturing line 10, first, as shown in FIG. 7 and FIG. 8, the heating unit 61 is arranged in a position between the upstream pinch roll device 38 and the tension control device 39 in the X direction conveying route R31X. In the case where the heating unit 61 is arranged in the position, the heating unit 61 is in the state of being arranged in a position that is directly above the main conveying route R11 of the main line 11, and thus the heating unit 61 is unlikely to have a thermal influence on the intermediate products 1*m* and so on in the main conveying route R11. Also, when making the modification, the hot air supplying device 67 is also arranged in a position that is displaced from the main conveying route R11 in the Y direction. By arranging the hot air supplying device 67 in the position, it is also possible to prevent the hot air supplying device 67 from having a thermal influence on the intermediate products 1*m* and so on in the main conveying route R11.

Other Embodiments

Although embodiments of the present invention have been described above, the above embodiments are for facilitating understanding of the present invention and is not for interpreting the present invention in a limiting manner. Also, modifications and improvements that can be made without departing from the gist of the present invention, as well as equivalents thereof are, needless to say, encompassed within the present invention. For example, modifications such as the following are possible.

Although the manufacturing line 10 for pet sheets 1 is given as an example of the apparatus for manufacturing an absorbent article in the above embodiments, there is no limitation whatsoever to this. For example, the concept of the present invention may be applied to an apparatus for manufacturing a diaper or a sanitary napkin. If this is the case, for both the diaper and the sanitary napkin, a non-woven fabric for the top sheet can be given as an example of the part to be heated with the heating unit 61 of the bulk restoring device 60.

The part to be heated with the heating unit 61, however, is not limited in any way to a non-woven fabric for top sheets.

In other words, a non-woven fabric for the material of another component required to have bulkiness may be heated with the heating unit 61.

Although the non-woven fabric 3 (3*a*) having multiple straight line-shaped projection portions 3*p*, 3*p* . . . on one surface as shown in FIG. 1B is given as an example of the non-woven fabric 3 (3*a*) for the top sheet 3 (3*a*) in the above embodiments, there is no limitation whatsoever to this. For example, it may be a non-woven fabric in a normal mode, that is to say a non-woven fabric with approximately flat surfaces on both sides.

Although the heating unit 61 of the bulk restoring device 60 heats the non-woven fabric 3*a* in both the outgoing route and the return route as shown in FIG. 2 in the above embodiments, there is no limitation whatsoever to this. For example, in the case where the bulk is sufficiently restored in only either the outgoing route or the return route, either the outgoing route blast opening 63Na or the return route blast opening 63Nb may be omitted. Conversely, if bulk restoration is not sufficient with merely two paths, namely the outgoing route and the return route, multiple heating units 61 may be provided rather than merely one, and the non-woven fabric 3*a* may be heated in three or more paths. Note that providing the blast openings 63Na and 63Nb in correspondence with the outgoing route and the return route is preferable due to shortening the dimension of the heating unit 61 in the lengthwise direction while also reliably ensuring a conveying route length for the non-woven fabric 3*a* that is needed for bulk restoration.

Although the heating unit 61 is configured in a system different from existing air-through systems as shown in FIGS. 6A and 6B in the above embodiments, there is no limitation whatsoever to this. Specifically, the heating unit may be configured in an existing air-through system. Note that a heating unit configured in an existing air-through system is as follows, for example. The heating unit has a hot air blast opening provided so as to oppose one of both surfaces of the non-woven fabric 3*a* conveyed along the conveying direction, and a hot air suction opening provided so as to oppose the other one of both surfaces. The blast opening and the suction opening forma streamline in which hot air blasted from the blast opening is sucked with the suction opening, and thus the hot air heats the non-woven fabric 3*a* as it passes through the non-woven fabric 3*a* in the thickness direction.

Note that a suction belt conveyor device, a suction drum device, and the like can be given as examples of the conveying mechanism that conveys the non-woven fabric 3*a* in the conveying direction. Specifically, the suction belt conveyor device conveys the non-woven fabric 3*a* in the state of being placed on the outer circumferential surface of an endless belt that is driven to revolve, and due to multiple suction holes being provided in the outer circumferential surface, the suction holes function as the above-described suction openings that suction the hot air.

Also, the suction drum device conveys the non-woven fabric 3*a* in the state of being wound around the outer circumferential surface of a rotating drum that is driven to rotate, and due to multiple suction holes being provided in the outer circumferential surface, the suction holes function as the above-described suction openings that suction the hot air.

Figure 9:
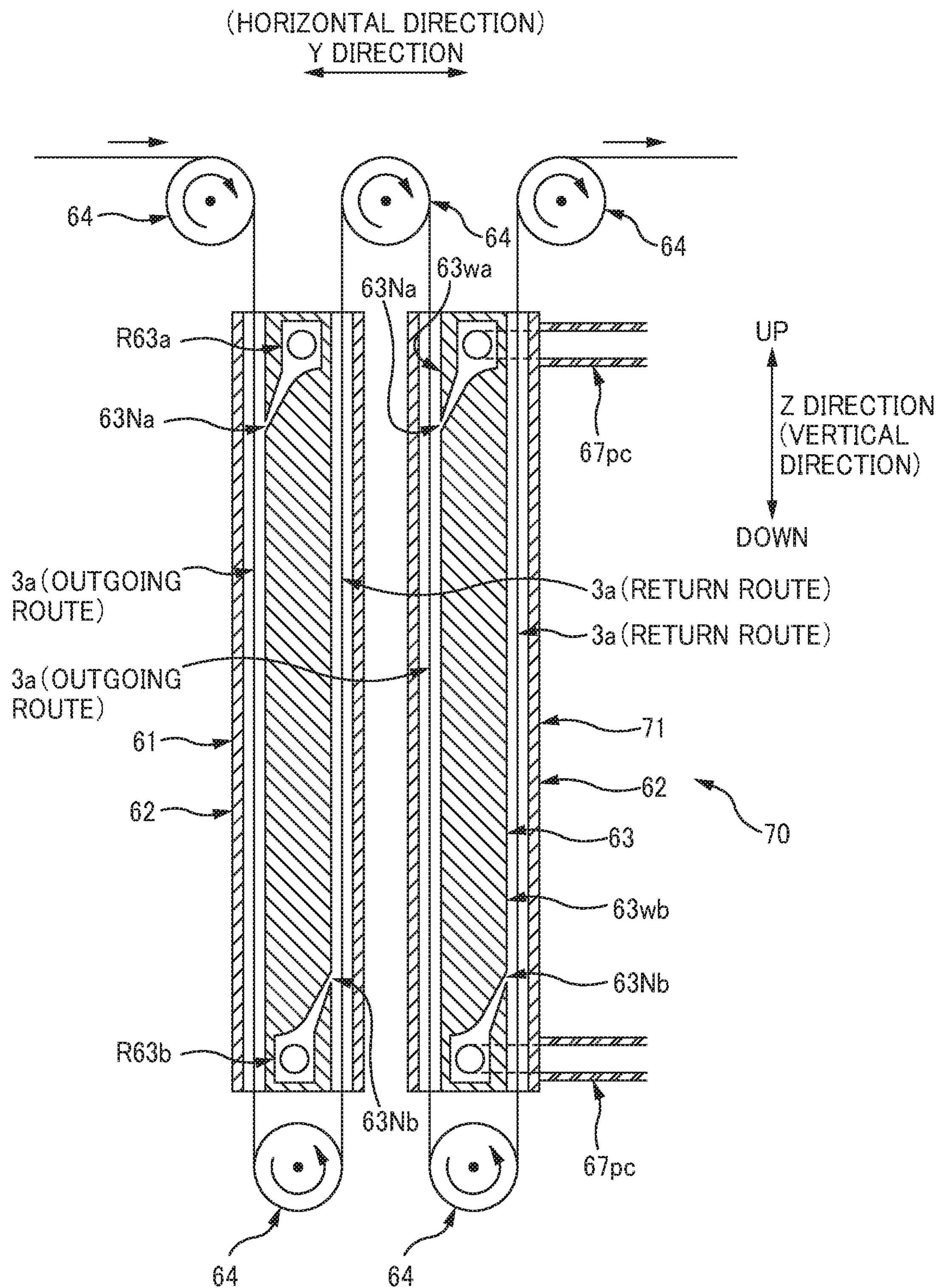
FIG. 9 is a schematic cross-sectional view of a cooling unit 71 added immediately downstream of a heating unit 61.

Although the non-woven fabric 3*a* that has passed through the heating unit 61 of the bulk restoring device 60 undergoes so-called natural cooling in the above embodiments, depending on the case, a cooling device 70 that forcibly cools the non-woven fabric 3*a* in a position on the immediately downstream side of the heating unit 61 may be added as shown in FIG. 9.

Specifically, the cooling device 70 is arranged in a position on the immediately downstream side of the heating unit 61, and has a cooling unit 71 that blows cooling wind on the non-woven fabric 3*a* in order to cool it, and a wind supplying device (not shown) that supplies cooling wind to the cooling unit 71.

In the case where the non-woven fabric 3*a* is cooled with the cooling wind blasted from the cooling unit 71, it is possible to reliably prevent the non-woven fabric 3*a* from having a thermal influence on the intermediate products 1*m* and the devices 14, 15, and so on in the main conveying route R11 of the main line 11.

It should be noted that a configuration similar to that of the previously-described heating unit 61 can be given as an example of the cooling unit 71. Specifically, the cooling unit 71 has a case member 62, a partition member 63, and guide rollers 64, 64, 64, similar to the heating unit 61. However, wind with a temperature capable of cooling the non-woven fabric 3*a* is blasted from slit-shaped blast openings 63Na and 63Nb provided in both wall surfaces 63*wa* and 63*wb* of the partition member 63. In other words, for example, room-temperature wind or cool wind with a temperature lower than room temperature is supplied from the wind supplying device to the blast openings 63Na and 63Nb via an appropriate pipe member 67*pc*. For this reason, the wind supplying device has at least a blower, and desirably has a cooler that cools the wind generated with the blower. Note that the above-described wind can cool the non-woven fabric 3*a* in the case where its temperature is lower than the temperature of the non-woven fabric 3*a* immediately after exiting the case member 62 of the heating unit 61, and thus may be higher than room temperature (20° C.±15° C.), such as being any value in the range of 5° C. to 50° C., for example, or may be set higher than this range depending on the situation.

It should be noted that according to the cooling unit 71 having this configuration, the cooling wind blasted from the blast openings 63Na and 63Nb flows over the surface of the non-woven fabric 3*a*, thus effectively preventing the non-woven fabric 3*a* from becoming compressed in the thickness direction. Accordingly, the loss of the restored bulk due to the wind is effectively avoided.

Although the hot air that has flowed through the outgoing route and return route spaces SP62*a* and SP62*b* is discharged as-is through the exits 62*aout* and 62*bout* for the non-woven fabric 3*a* in the case member 62 in the above embodiments (FIG. 6A), from the viewpoint of energy reuse and from the viewpoint of mitigating adverse effects from the hot air on other devices and other members in the vicinity, the hot air that has flowed through the spaces SP62*a* and SP62*b* may be recovered and returned to the intake-side portion 67*bs* of the blower 67*b*. For example, as shown in the schematic cross-sectional view in FIG. 10, a configuration is possible in which openings 63*ha* and 63*hb* are provided in portions of the partition member 63 on the downstream side in the conveying direction, and pipe end opening portions on one side of recovery pipe members 69 are connected to the openings 63*ha* and 63*hb*, thus putting the spaces inside the pipe members 69 into communication with at least one out of a downstream end portion SP62*ae* of the outgoing route space SP62*a* and a downstream end portion SP62*be* of the return route space SP62*b*, and putting the pipe end opening portions on the other side of the pipe members 69 into communication with the intake-side portion 67*bs* of the blower 67*b*.

Figure 10:
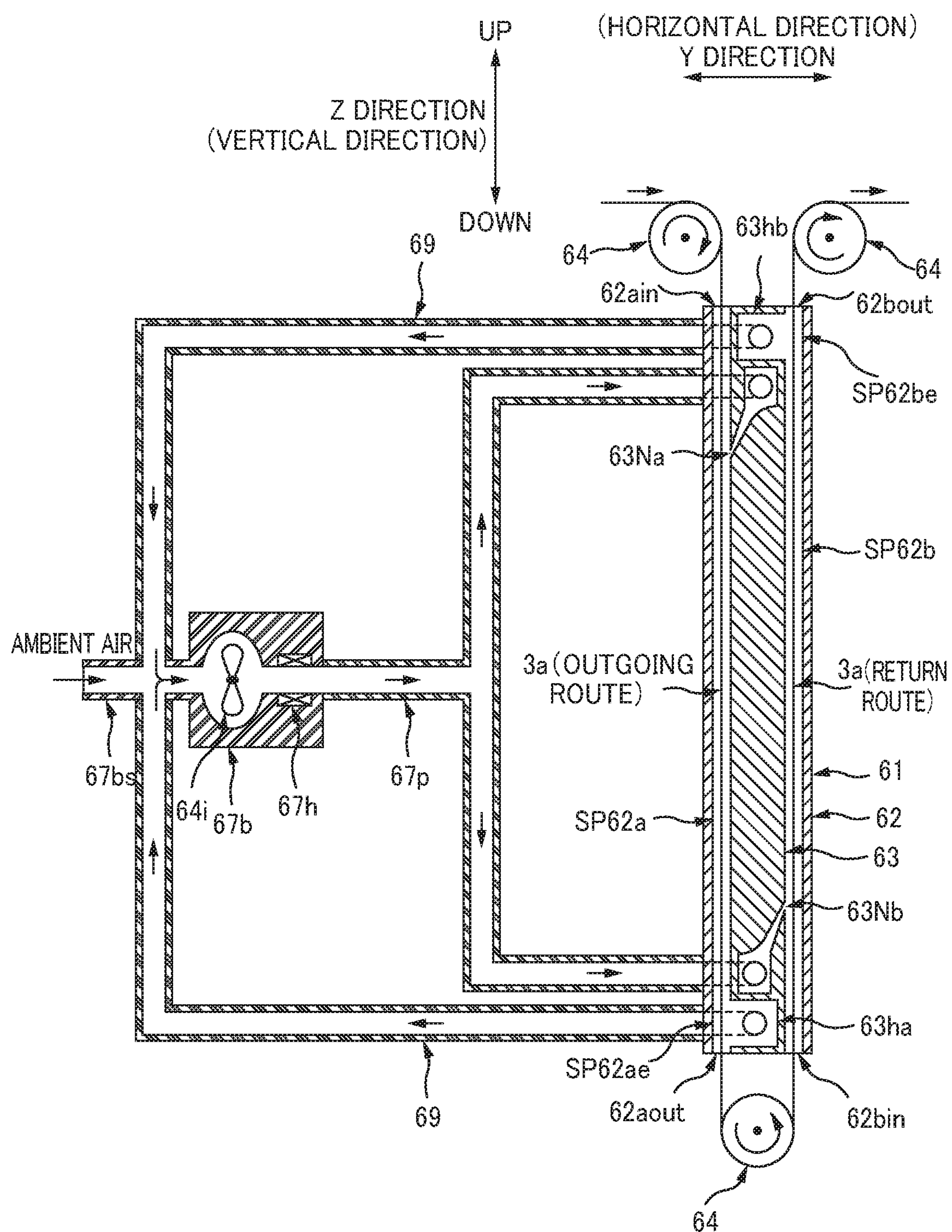
FIG. 10 is a schematic cross-sectional view of a configuration for recovering hot air flowing through outgoing route and return route spaces SP62*a* and SP62*b* within the heating unit 61 and returning it to an intake-side portion 67*bs* of a blower 67*b*.

It should be noted that in the case of the example in FIG. 10, there is a risk of foreign objects such as fiber scraps from the non-woven fabric 3*a* being sent through the recovery pipe members 69 to the heater 67*h* in the blower 67*b* and becoming fused thereto. For this reason, it is preferable that a mesh-like foreign object suction prevention filter member having a predetermined mesh, for example, is inserted between the recovery pipe members 69 and the intake-side portion 67*bs* of the blower 67*b*. Note that in the case of the example in FIG. 6A as well, there is a risk of foreign objects such as paper dust in the manufacturing line 10 becoming mixed with the ambient air and sucked through the intake-side portion 67*bs*, and thus it is preferable that the same type of filter member is provided in the intake-side portion 67*bs*.

In the above embodiments, as shown in FIG. 6A, the outgoing route blast opening 63Na is provided in the portion of the outgoing route wall surface 63*wa* on the upstream side in the outgoing route, and the return route blast opening 63Nb is provided in the portion of the outgoing route wall surface 63*wb* on the upstream side in the return route, but there is no limitation whatsoever to this.

For example, a configuration is possible in which the outgoing route blast opening 63Na is provided in a portion of the outgoing route wall surface 63*wa* on the downstream side in the outgoing route (this corresponds to the "exit-side portion of the case member") , and the return route blast opening 63Nb is provided in a portion of the return route wall surface 63*wb* on the downstream side in the return route (this corresponds to the "exit-side portion of the case member"). Note that in this case, both of the outgoing route and return route blast openings 63Na and 63Nb are formed so as to blast hot air toward the upstream side in the conveying direction with an acute angle of inclination relative to one of the two surfaces of the non-woven fabric 3*a*. Accordingly, the hot air blasted from the outgoing route blast opening 63Na comes into contact with the surface of the non-woven fabric 3*a* with a velocity component in a direction toward the upstream side in the conveying direction, continues to flow over the surface of the non-woven fabric 3*a* toward the upstream side, and is ultimately discharged to the outside through the outgoing route entrance 62*ain* located the most upstream in the outgoing route space SP62*a*. Also, the hot air blasted from the return route blast opening 63Nb comes into contact with the surface of the non-woven fabric 3*a* with a velocity component in a direction toward the upstream side in the conveying direction, continues to flow over the surface of the non-woven fabric 3*a* toward the upstream side, and is discharged to the outside from the return route entrance 62*bin* located the most upstream in the conveying direction in the return route space SP62*b*. It should be noted that the same applies to the above-described cooling unit 71 as well.

Although a solid member basically not having a space therein other than the pressure chambers R63*a* and R63*b* is used as the material for the partition member 63 in the above embodiments, there is no limitation whatsoever to this. For example, for the purpose of weight reduction or the like, a hollow member having a space therein may be used. One example that can be given for this hollow member is a combined member having, for example, a stainless steel flat plate member (not shown) that forms the outgoing route wall surface 63*wa* in FIG. 6A, a stainless steel flat plate member (not shown) that forms the return route wall surface 63*wb*, and a rectangular column member (not shown) that is inserted between these flat plate members and connects these two flat plate members.

Although the X direction is given as an example of the first direction and the Y direction is given as an example of the Y direction, and the X direction and the Y direction are orthogonal to each other in the above embodiments, there is no limitation whatsoever to this. Specifically, they only need to intersect each other within the horizontal plane.

Figure 11:
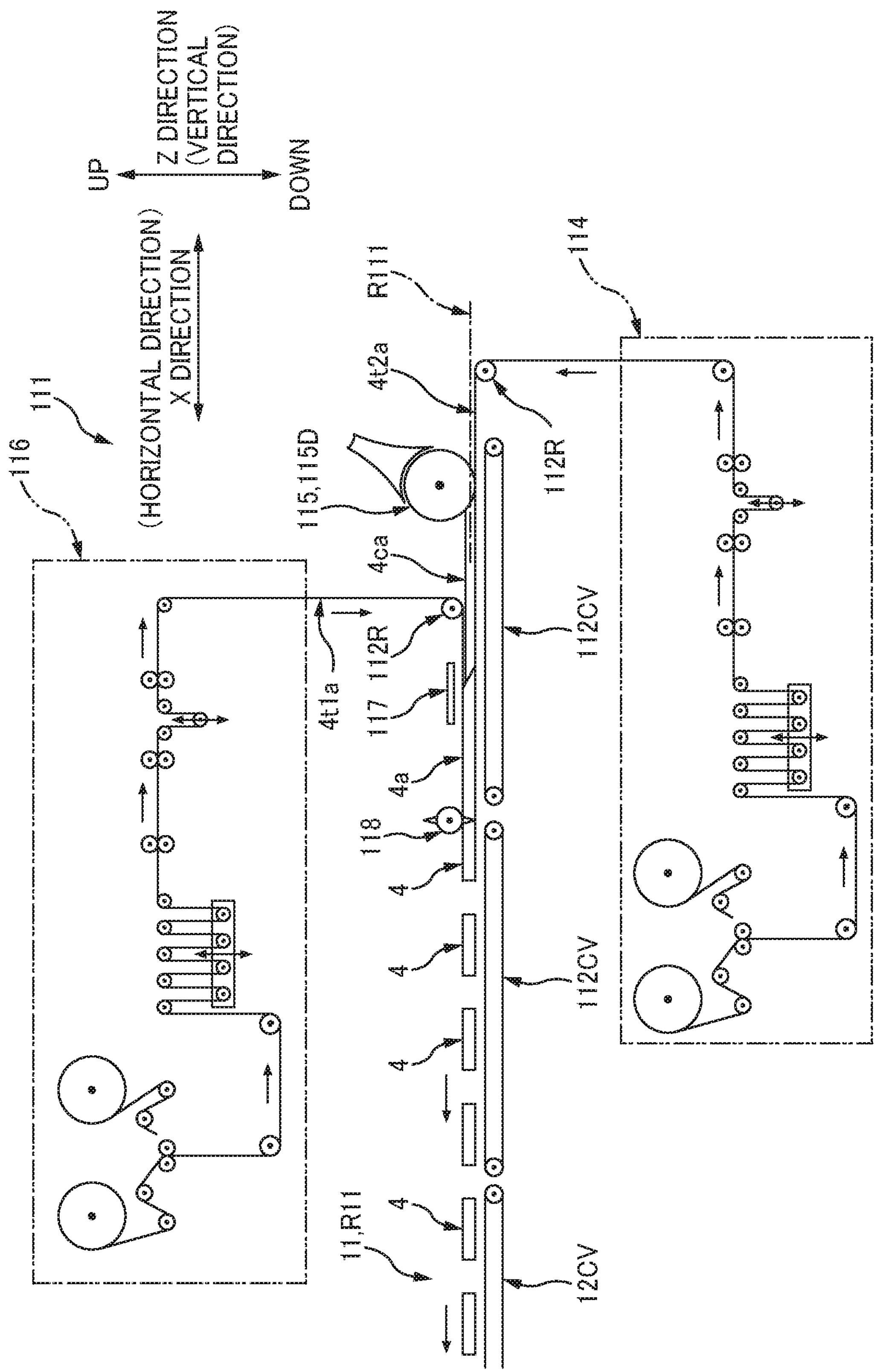
FIG. 11 is a schematic side view of an absorbent body manufacturing apparatus 111.

Although the main line 11 in FIG. 2 does not have an absorbent body manufacturing apparatus 111 for manufacturing an absorbent body 4 in the above embodiments, the main line 11 may have the absorbent body manufacturing apparatus 111. FIG. 11 is a schematic side view of the absorbent body manufacturing apparatus 111. A conveying route R111 of the absorbent body manufacturing apparatus 111 also has a straight line shape along the X direction in plan view, and the conveying route R111 is connected straight to the upstream side of the main conveying route R11 of the above-described main line 11. In the conveying route R111 as well, appropriate conveying devices such as a conveyor 112CV and a conveying roller 112R are provided to convey the intermediate products 1*m* related to the pet sheet 1 such as a continuous sheet 4*t*2*a* of non-skin-side covering sheets 4*t*2 and a continuous body 4*a* of absorbent bodies 4.

Furthermore, the conveying route R111 is provided with a non-skin-side covering sheet supplying device 114 that supplies a strip-shaped continuous sheet 4*t*2*a* (simply referred to hereinafter as the non-skin-side covering sheet 4*t*2*a*) of non-skin-side covering sheets 4*t*2 to the route R111; a fiber stacking drum device 115 that stacks a continuous body 4*ca* of the absorbent cores 4*c* on the upper surface of the non-skin-side covering sheet 4*t*2*a;* a skin-side covering sheet supplying device 116 that supplies a strip-shaped continuous sheet 4*t*1*a* (simply referred to hereinafter as the skin-side covering sheet 4_t_1_a_) of skin-side covering sheets 4_t_1 from above the continuous body 4_ca_ of absorbent cores 4_c;_ a fold-back guide device 117 that folds back each end portion of the non-skin-side covering sheet 4_t_2_a_ in the Y direction so as to cover the skin-side covering sheet 4_t_1_a;_ and a rotary cutter device 118 that generates absorbent bodies 4 by cutting the continuous body 4_a_ of absorbent bodies 4 formed by folding back each end portion of the non-skin-side covering sheet 4_t_2_a_, lined up in the stated order from upstream to downstream in the conveying direction. The conveying velocity value of absorbent bodies 4 in the conveyor 112CV at a position immediately downstream of the rotary cutter device 118 is set higher than the conveying velocity value of the absorbent bodies 4 in the rotary cutter device 118, and accordingly a gap is formed between absorbent bodies 4, 4, that are adjacent in the conveying direction, and the absorbent bodies 4, 4 . . . are sent to the main conveying route R11 of the main line 11 with gaps therebetween.

Note that the devices 114, 115, 116, 117, and 118 are also supported by the aforementioned panel board of the main conveying route R11, for example.

Here, the non-skin-side covering sheet supplying device 114 and the skin-side covering sheet supplying device 116 can each obviously be realized using the same types of devices as the devices 95, 95, 96, and so on provided in the sub line 90 for back sheets 5_a_ in FIG. 2, and thus the description thereof is omitted.

The fiber stacking drum device 115 can also obviously be realized using a rotation drum 115D that rotates and has liquid-absorbent fibers and a SAP sucking function on the outer circumferential surface, and thus the description thereof is omitted as well.

Furthermore, the fold-back guide device 117 can also obviously be realized by arranging an appropriate plate member on both sides in the Y direction, and thus the description thereof is omitted.

The rotary cutter device 118 can also obviously be realized using a device of the same type as the rotary cutter device 18 (FIG. 2) provided in the main conveying route R11 of the existing main line 11, and thus the description thereof is omitted as well.

Although the fiber stacking drum device 115 in the above absorbent body manufacturing apparatus 111 manufactures the continuous body 4_ca_ of absorbent cores 4_c_, there is no limitation whatsoever to this. Specifically, the fiber stacking drum device 115 may manufacture multiple absorbent cores 4_c_, 4_c_ . . . in the state of being lined up with gaps therebetween in the conveying direction.

Also, in some case, one or multiple press devices (not shown) may be provided in a position between the fold-back guide device 117 and the rotary cutter device 118 in the conveying route R111, and the continuous body 4_a_ of absorbent bodies 4 may be pressed by using the press device in the vertical direction, which is the thickness direction. Note that a configuration having a pair of upper and lower rolls that rotate can be given as an example of the press device.

The invention claimed is:

1. An absorbent article manufacturing apparatus, comprising:

a first conveying route arranged in a straight line along a first direction in a plan view;

a second conveying route configured to convey a non-woven fabric in a second direction that intersects the first direction in the plan view, the non-woven fabric being a strip shape and serving as a part of an absorbent article;

a plurality of processing devices configured to process an intermediate product of the absorbent article that is conveyed along the first conveying route; and a heating unit configured to restore bulk of the non-woven fabric through heating the non-woven fabric by blowing hot air onto the non-woven fabric while conveying the non-woven fabric along a direction in which the non-woven fabric is continuous, wherein in the plan view, the heating unit is arranged in a position that is displaced from the first conveying route in the second direction, the heating unit has a case member including a space divided into (i) an outgoing route space having an outgoing route entrance and an outgoing route exit and (ii) a return route space having a return route entrance and a return route exit, the outgoing route entrance and the return route exit for the non-woven fabric are formed in a first end portion of the case member, the outgoing route exit and the return route entrance for the non-woven fabric are formed in a second end portion of the case member, the first and second end portions opposing each other in a lengthwise direction of the case member, the case member further includes a first blast opening configured to blast the hot air into the outgoing route space toward the outgoing route exit, and a second blast opening configured to blast the hot air into the return route space toward the return route exit, the outgoing route exit and the return route exit define first and second discharge ports, respectively, the first and second discharge ports being configured to discharge, from the case member, the hot air that has flowed while being in contact with one surface of two surfaces of the non-woven fabric, and the apparatus is configured to input the non-woven fabric from the second conveying route to the first conveying route, after the non-woven fabric has been heated by the heating unit and the bulk of the non-woven fabric has been restored.

2. The absorbent article manufacturing apparatus according to claim 1, further comprising:

a cooling unit configured to cool the non-woven fabric that has been heated by the heating unit, before the non-woven fabric is input to the first conveying route, wherein the cooling unit has a further case member including third and fourth end portions opposing each other in a lengthwise direction of the further case member, the further case member has a blast opening configured to blast cooling air, from the third end portion, into a space inside the further case member toward the fourth end portion and the fourth end portion has a third discharge port configured to discharge, from the further case member, the air that has flowed inside the further case member while being in contact with one surface of the two surfaces of the non-woven fabric.

3. The absorbent article manufacturing apparatus according to claim 1, wherein the heating unit is arranged in the position that does not overlap with the first conveying route in the plan view.

4. The absorbent article manufacturing apparatus according to claim 1, further comprising:
a turn bar arranged at an intersection point of the first and second conveying routes to transfer the non-woven fabric from the second conveying route to the first conveying route.

5. The absorbent article manufacturing apparatus according to claim 1, wherein
the case member includes a partition member dividing the space of the case member into the outgoing route space and the return route space, and
the partition member is configured to prevent the hot air from travelling between the outgoing route space and the return route space.

6. The absorbent article manufacturing apparatus according to claim 5, wherein
the first and second blast openings are slits arranged in the partitioning member.

7. The absorbent article manufacturing apparatus according to claim 1, wherein the apparatus is configured to move the non-woven fabric into the outgoing route space from the outgoing route entrance to the outgoing route exit and then move the non-woven fabric into the return route space from the return route entrance to the return route exit.

8. An absorbent article manufacturing method, comprising:
conveying an intermediate product of an absorbent article in a first conveying route arranged in a straight line along a first direction in a plan view;
processing, by a plurality of processing devices, the intermediate product conveyed along the first conveying route;
conveying a non-woven fabric in a second conveying route along a second direction that intersects the first direction in the plan view, the non-woven fabric being a strip shape and serving as a part of an absorbent article;
restoring, by a heating unit, bulk of the non-woven fabric through heating the non-woven fabric by blowing hot air onto the non-woven fabric with the heating unit, while conveying the non-woven fabric along a direction in which the non-woven fabric is continuous; and
inputting the non-woven fabric from the second conveying route to the first conveying route, after the non-woven fabric has been heated by the heating unit and the bulk of the non-woven fabric has been restored,
wherein
in the plan view, the heating unit is arranged in a position that is displaced from the first conveying route in the second direction,
the heating unit has a case member including a space divided into (i) an outgoing route space having an outgoing route entrance and an outgoing route exit and (ii) a return route space having a return route entrance and a return route exit,
the outgoing route entrance and the return route exit for the non-woven fabric are formed in a first end portion of the case member,
the outgoing route exit and the return route entrance for the non-woven fabric are formed in a second end portion of the case member, the first and second end portions opposing each other in a lengthwise direction of the case member,
the case member further includes
a first blast opening that blasts the hot air into the outgoing route space toward the outgoing route exit, and
a second blast opening that blasts the hot air into the return route space toward the return route exit,
the outgoing route exit and the return route exit define first and second discharge ports, respectively, the first and second discharge ports discharging, from the case member, the hot air that has flowed while being in contact with one surface of two surfaces of the non-woven fabric.

* * * * *